United States Patent
Burckhardt

(10) Patent No.: US 7,629,433 B2
(45) Date of Patent: *Dec. 8, 2009

(54) COMPOUNDS CONTAINING ALDIMINE

(75) Inventor: Urs Burckhardt, Zurich (CH)

(73) Assignee: Sika Technology AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/992,134

(22) PCT Filed: Sep. 29, 2006

(86) PCT No.: PCT/EP2006/066925

§ 371 (c)(1),
(2), (4) Date: Apr. 21, 2008

(87) PCT Pub. No.: WO2007/036572

PCT Pub. Date: Apr. 5, 2007

(65) Prior Publication Data

US 2009/0099333 A1    Apr. 16, 2009

(30) Foreign Application Priority Data

Sep. 30, 2005  (EP) .................................. 05109111

(51) Int. Cl.
*C08G 69/08* (2006.01)
(52) U.S. Cl. ...................... 528/310; 560/129; 549/551; 548/546
(58) Field of Classification Search ................... 528/310
See application file for complete search history.

(56) References Cited

U.S. PATENT DOCUMENTS

| 3,493,543 | A | 2/1970 | Nazy et al. |
| 3,554,974 | A | 1/1971 | Mommaerts et al. |
| 4,108,842 | A | 8/1978 | Konig et al. |
| 4,224,417 | A | 9/1980 | Hajek et al. |
| 4,404,379 | A | 9/1983 | Hajek et al. |
| 4,469,831 | A | 9/1984 | Bueltjer et al. |
| 4,853,454 | A | 8/1989 | Merger et al. |
| 5,087,661 | A | 2/1992 | Aoki et al. |
| 5,880,180 | A * | 3/1999 | Smith ......................... 523/508 |
| 6,136,942 | A | 10/2000 | Pfenninger et al. |
| 2006/0149025 | A1 * | 7/2006 | Burckhardt .................. 528/230 |

FOREIGN PATENT DOCUMENTS

| EP | 398561 | * 11/1990 |
| EP | 1 384 709 A1 | 1/2004 |
| EP | 1 544 204 A1 | 6/2005 |
| WO | WO 2004/013088 A1 | 2/2004 |

* cited by examiner

*Primary Examiner*—Randy Gulakowski
*Assistant Examiner*—Shane Fang
(74) *Attorney, Agent, or Firm*—Oliff & Berridge, PLC

(57) ABSTRACT

The invention relates to compounds of formula (I) which contain aldimine, and to the use thereof. Said compounds which contain aldimines are characterized in that they are odor-less and during hydrolysis the odor-free aldehydes are separated. They are used, therefor, as sources for aldehydes. They can also be used in cross-linking reactions.

21 Claims, No Drawings

COMPOUNDS CONTAINING ALDIMINE

FIELD OF THE INVENTION

The invention relates to the field of aldimines and aldimine-containing compounds.

PRIOR ART

Aldimines are condensates of amines and aldehydes and constitute a class of substance which has long been known. On contact with water, aldimines can be hydrolyzed to the corresponding amines and aldehydes, while they are stable in the absence of water. Owing to this peculiarity, they can be used as a bound or protected form of amines or aldehydes. Thus, aldimines are used, for example, in polyurethane chemistry, where they serve as crosslinking agents which can be activated by moisture, so-called "latent amines" or "latent curing agents", for isocyanate-containing plastic precursors. The use of an aldimine as a latent curing agent in isocyanate-containing systems has two advantages: firstly, the formation of undesired gas bubbles in the cured plastic can be avoided since the curing via the latent amine—in contrast to the direct reaction of the isocyanate with moisture—does not take place with liberation of carbon dioxide ($CO_2$); secondly, it is possible to achieve high curing rates. However, the use of an aldimine in a storable isocyanate-containing plastic precursor harbors the danger of reducing its shelf-like by premature reaction between aldimino and isocyanate groups. For example, U.S. Pat. No. 4,469,831, U.S. Pat. No. 4,853,454 and U.S. Pat. No. 5,087,661 describe compositions of polyisocyanates and polyaldimines which crosslink and hence cure under the influence of moisture to give high molecular weight plastics. However, such polyaldimines eliminate strongly smelling aldehydes on hydrolysis. WO 2004/013088 A1 describes odorless polyaldimines which are prepared from the reaction of primary polyamines and odorless aldehydes.

Aldimines which have additional functional groups are known. U.S. Pat. No. 4,224,417 describes, for example, hydroxyaldimines and their reaction products with polyisocyanates. U.S. Pat. No. 3,493,543, U.S. Pat. No. 3,554,974, U.S. Pat. No. 4,108,842, U.S. Pat. No. 4,404,379 and U.S. Pat. No. 6,136,942 describe aminoaldimines or cycloaminals as a tautomeric form thereof, their reaction products with polyisocyanates and the use thereof as latent curing agents for isocyanate-containing compositions which cure rapidly and without bubbles under the influence of moisture. The compositions described in said publications have, however, the disadvantage of possessing a greatly limited shelf-life. This is due to the fact that the protected amino groups which are present in the form of aldimino or cycloaminal groups in the aldimines described or their reaction products are not completely inert to isocyanate groups but react with them gradually, in particular with the reactive aromatic isocyanate groups, even in the absence of moisture and thus cause an increase in viscosity which can make the composition unusable after only a short time. A further disadvantage of the described aldimines containing an active hydrogen, and reaction products thereof and compositions obtained therefrom, is that they exhibit strong odor formation on contact with moisture, owing to the intensely odorous aldehydes liberated on hydrolysis of the aldimino groups, and can therefore be used only to a limited extent, in particular in interior rooms.

SUMMARY OF THE INVENTION

It was therefore an object of the present invention to provide aldimines which are odorless, eliminate aldehydes which are likewise odorless, can be used in particular for plastic precursors which have isocyanate groups and are distinguished by an improved shelf-life.

Surprisingly, it has been found that aldimine-containing compounds as claimed in claim 1 achieve this object. It has furthermore been found that said aldimine-containing compounds represent substances which have extraordinary properties and which can be used as a plastic precursor or as a constituent of a plastic precursor. They can be prepared in a simple manner and have a large range of structural features and chemically reactive groups. They therefore have broad application possibilities in reactive systems. Isocyanate-containing compositions which were prepared using these aldimine-containing compounds have a long shelf-life. Such compositions cure rapidly and without bubble formation under the influence of moisture, are odorless and are suitable, for example, as adhesives, sealants, coatings or coverings with good mechanical properties.

DESCRIPTION OF THE PREFERRED EMBODIMENTS

The invention relates to aldimine-containing compounds of the formula (I)

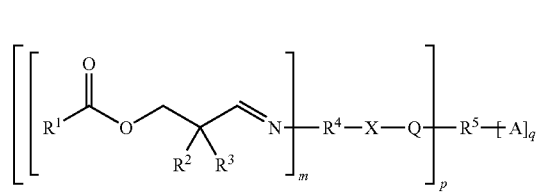

Here, m is an integer from 1 to 4, p is an integer from 1 to 6 and q is an integer from 0 to 5, with the proviso that the sum of p and q has a value of from 2 to 6. Furthermore, the substituent $R^1$ is either a monovalent hydrocarbon radical having 6 to 30 C atoms which optionally has at least one heteroatom, in particular in the form of ether oxygen, or $R^1$ is a substituent of the formula (II).

Here, the substituent $R^6$ is a divalent hydrocarbon radical having 2 to 20 C atoms which optionally has at least one heteroatom, in particular in the form of ether oxygen. The substituent $R^7$ is a monovalent hydrocarbon radical having 1 to 20 C atoms.

Furthermore, $R^2$ and $R^3$ are either two substituents which are independent of one another and which in each case are a monovalent hydrocarbon radical having 1 to 12 C atoms, or $R^2$ and $R^3$ together form a single substituent which is a divalent hydrocarbon radical which has 4 to 20 C atoms and which is part of a carbocyclic ring having 5 to 8, preferably 6, C atoms, this carbocyclic ring optionally being substituted.

Furthermore, the substituent $R^4$ is an (m+1)-valent hydrocarbon radical which has 2 to 12 C atoms and optionally contains at least one heteroatom, in particular in the form of ether oxygen or tertiary amine nitrogen.

Furthermore, X is O, S or N—$R^8$, $R^8$ here being either a monovalent hydrocarbon radical which has 1 to 20 C atoms and optionally has at least one carboxylic acid ester, nitrile, nitro, phosphonic acid ester, sulfone or sulfonic acid ester group, or is a substituent of the formula (III).

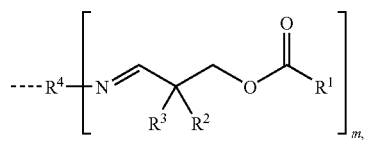

(III)

Furthermore, A is a reactive group which is selected from the group consisting of

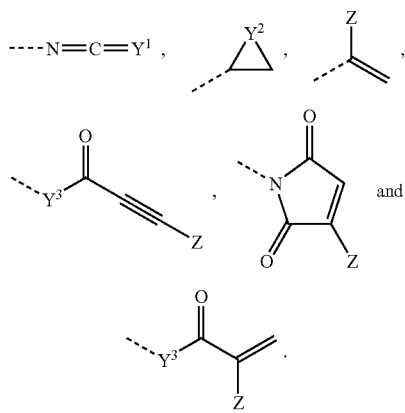

Here, the substituent $Y^1$ is O or S, $Y^2$ is O, S or N—H, Z is H or $CH_3$ and $Y^3$ is O or N—H. Furthermore, $R^5$ is either a (p+q)-valent organic radical. Such a radical optionally contains heteroatoms and can be obtained by removing p+q radicals A from $R^5$-$[A]_{p+q}$. Or the substituent $R^5$ is N, $NR^{14}$, O, OC(O)O, Si, $P(O)O_3$ or $SO_2$. Here, the substituent $R^{14}$ is a monovalent hydrocarbon radical having 1 to 20 C atoms. Finally, Q is a substituent which is selected from the group consisting of

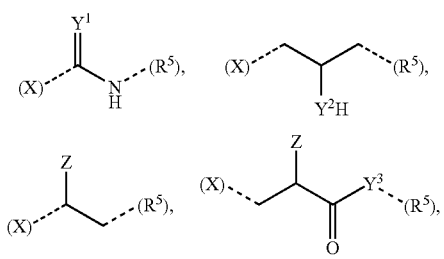

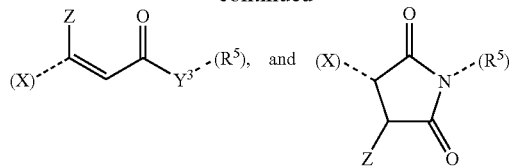

The dashed lines in the formulae are the bonds to the stated substituents.

The aldimine-containing compound of the formula (I) can be prepared by reacting at least one aldimine of the formula (XI) containing an active hydrogen with at least one compound D which carries more than one reactive group which can undergo addition reactions with the group XH. That reactive group XH of the aldimine of the formula (XI) which carries the active hydrogen reacts in an addition reaction with one or more reactive groups of the compound D to give an aldimine-containing compound also referred to below as "adduct". In the present document, the term "active hydrogen" designates a deprotonatable hydrogen atom bonded to a nitrogen, oxygen or sulfur atom. The term "reactive group containing an active hydrogen" designates a functional group having an active hydrogen, in particular a primary or secondary amino group, a hydroxyl group, a mercapto group or a urea group. Attributes of substances such as "aldimine-containing" or "isocyanate-containing" indicate that the designated functional groups, that is to say, aldimino groups or isocyanate groups, are present in the substances.

$$\left[ R^1 \underset{\substack{\\}}{\overset{O}{\|}} O \underset{R^2}{\overset{}{-}} \underset{R^3}{\overset{}{-}} N \right]_m R^4 - XH \quad (XI)$$

The substituents $R^1$, $R^2$, $R^3$, $R^4$ and X, and the index m have the meanings already disclosed for the aldimine-containing compound of the formula (I).

The aldimine of the formula (XI) can be prepared from at least one sterically hindered aliphatic aldehyde A and at least one aliphatic amine B, corresponding to the formula $[H_2N]_m$—$R^4$—XH, which, in addition to one or more primary amino groups, also has a further reactive group containing an active hydrogen.

The reaction between the aldehyde A and the amine B takes place in a condensation reaction with elimination of water. Such condensation reactions are very well known and are described, for example, in Houben-Weyl, "Methoden der organischen Chemie [Methods of Organic Chemistry]", vol. XI/2, page 73 et seq. Here, the aldehyde A is used stoichiometrically or in stoichiometric excess relative to the primary amino groups of the amine B. Usually, such condensation reactions are carried out in the presence of a solvent, by means of which the water forming in the reaction is removed azeotropically. For the preparation of the aldimines of the formula (XI), however, a preparation process without the use of solvents is preferred, the water formed in the condensation being removed directly from the reaction mixture by application of a vacuum. As a result of the solvent-free preparation, there is no need to distill off the solvent after the preparation is complete, which simplifies the preparation process. In addition, the aldimine is thus free of solvent residues which might cause a troublesome odor.

For the preparation of the aldimine of the formula (XI), at least one sterically hindered aliphatic aldehyde A of the formula (IV) is used.

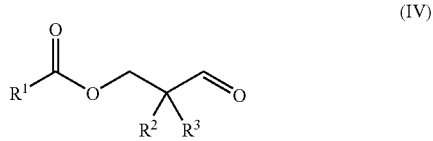

(IV)

In the formula (IV), $R^1$, $R^2$ and $R^3$ have the same meaning as described for formula (I).

The aldehyde A is odorless. An "odorless" substance is understood as meaning a substance which has such little odor that it cannot be smelt by most human individuals, i.e. is not perceptible to the nose.

The aldehyde A is prepared, for example, from a carboxylic acid $R^1$—COOH and a β-hydroxyaldehyde of the formula (V) in an esterification reaction. This esterification can be effected by known methods, described, for example, in Houben-Weyl, "Methoden der organischen Chemie [Methods of Organic Chemistry]", vol. VIII, pages 516-528. The β-hydroxyaldehyde of the formula (V) is obtained, for example, in a crossed aldol addition from formaldehyde (or oligomeric forms of formaldehyde, such as paraformaldehyde or 1,3,5-trioxane) and an aldehyde of the formula (VI).

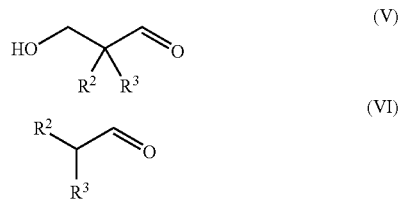

(V)

(VI)

In the formulae (V) and (VI), $R^2$ and $R^3$ have the same meaning as described for formula (I).

The preparation of the aldehyde A preferably takes place in the absence of a solvent. The β-hydroxyaldehyde of the formula (V) is reacted directly with the carboxylic acid without the use of solvents, the water formed in the esterification being removed in vacuo. It is furthermore preferred to carry out the aldol and esterification reactions leading to the aldehyde A from the parent substances in a common process step, as a one-pot reaction.

By way of example, the following may be mentioned as suitable carboxylic acids $R^1$—COOH for the esterification with the β-hydroxyaldehydes of the formula (V): saturated aliphatic carboxylic acids, such as oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid; monounsaturated aliphatic carboxylic acids, such as palmitoleic acid, oleic acid, erucic acid; polyunsaturated aliphatic carboxylic acids, such as linoleic acid, linolenic acid, elaeostearic acid, arachidonic acid; cycloaliphatic carboxylic acids, such as cyclohexanecarboxylic acid; arylaliphatic carboxylic acids, such as phenylacetic acid; aromatic carboxylic acids, such as benzoic acid, naphthoic acid, toluic acid, anisic acid; isomers of these acids; fatty acid mixtures from the industrial saponification of natural oils and fats, such as, for example, rapeseed oil, sunflower oil, linseed oil, olive oil, coconut oil, oil-palm kernel oil and oil-palm oil; and monoalkyl and monoaryl esters of dicarboxylic acids, as obtained from the monoesterification of dicarboxylic acids, such as succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydroterephthalic acid, 3,6,9-trioxaundecanedioic acid, and similar derivatives of polyethylene glycol, with alcohols, such as methanol, ethanol, propanol, butanol, higher homologues and isomers of these alcohols.

Caprylic acid, capric acid, lauric acid, myristic acid, palmitic acid, stearic acid, oleic acid, linoleic acid, linolenic acid, the isomers of these acids and industrial mixtures of fatty acids which contain these acids are preferred. Lauric acid is particularly preferred.

Suitable aldehydes of the formula (VI) for reaction with formaldehyde to give β-hydroxyaldehydes of the formula (V) are, for example, isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde, and diphenylacetaldehyde. Isobutyraldehyde is preferred.

Suitable β-hydroxyaldehydes of the formula (V) are, for example, the products from the reaction of formaldehyde with the aldehydes of the formula (VI) which are mentioned above as being suitable. 3-Hydroxypivalaldehyde is preferred.

The amine B is an aliphatic amine which, in addition to one or more primary amino groups, also has a further reactive group which contains an active hydrogen. In the present document, the term "primary amino group" designates an $NH_2$ group which is bonded to an organic radical, while the term "secondary amino group" designates an NH group which is bonded to two organic radicals. The term "aliphatic amine" designates compounds which contain at least one amino group which is bonded to an aliphatic, cycloaliphatic or arylaliphatic radical. They therefore differ from the aromatic amines in which the amino group is bonded directly to an aromatic radical, such as, for example, in aniline or 2-aminopyridine.

Suitable amines B are, for example, the compounds mentioned below:

aliphatic hydroxyamines, such as 2-aminoethanol, 2-methylaminoethanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol; derivatives of glycols, such as diethylene glycol, dipropylene glycol, dibutylene glycol and higher oligomers and polymers of these glycols, which carry a primary amino group, for example 2-(2-aminoethoxy)ethanol, triethylene glycol monoamine, α-(2-hydroxymethylethyl)-ω-(2-aminoethylethoxy)poly(oxy(methyl-1,2-ethanediyl)); derivatives of polyalkoxylated trihydric or higher-hydric alcohols or of polyalkoxylated diamines which carry one or more primary amino groups; products of the monocyanoethylation and subsequent hydrogenation of glycols, for example 3-(2-hydroxyethoxy)propylamine, 3-(2-(2-hydroxyethoxy)ethoxy)propylamine, 3-(6-hydroxyhexyloxy)propylamine;

aliphatic mercaptoamines, such as 2-aminoethanethiol (cysteamine), 3-aminopropanethiol, 4-amino-1-butanethiol, 6-amino-1-hexanethiol, 8-amino-1-octanethiol, 10-amino-1-decanethiol, 12-amino-1-dodecanethiol; aminothio sugars, such as 2-amino-2-deoxy-6-thioglucose;

di- or polyfunctional aliphatic amines which, in addition to one or more primary amino groups, carry a secondary amino group, such as N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, 3-(4-aminobutyl)piperidine, N-aminoethylpiperazine, diethylenetriamine (DETA), bishexamethylenetriamine (BHMT); di- and triamines from the cyanoethylation or cyanobutylation of primary mono- and diamines, for example N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, dipropylenetriamine (DPTA), N3-(3-aminopentyl)-1,3-pentanediamine, N5-(3-aminopropyl)-2-methyl-1,5-pentanediamine, N5-(3-amino-1-ethylpropyl)-2-methyl-1,5-pentanediamine, and fatty diamines, such as N-cocoalkyl-1,3-propanediamine, N-oleyl-1,3-propanediamine, N-soyaalkyl-1,3-propanediamine, N-tallowalkyl-1,3-propanediamine or N—($C_{16-22}$-alkyl)-1,3-propanediamine, as are obtainable, for example, under the trade name Duomeen® from Akzo Nobel; the products from the Michael-like addition reaction of aliphatic primary di- or polyamines with acrylonitrile, maleic or fumaric acid diesters, citraconic acid diesters, acrylic and methacrylic acid esters and itaconic acid diesters, reacted in the molar ratio 1:1;

trisubstituted ureas which carry one or more primary amino groups, such as N-(2-aminoethyl)ethyleneurea, N-(2-aminoethyl)propyleneurea or N-(2-aminoethyl)-N'-methylurea.

Particularly suitable aliphatic hydroxy- and mercaptoamines are those in which the primary amino group are separated from the hydroxyl or the mercapto group by a chain of at least 5 atoms or by a ring, as, for example, in 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol, 2-(2-aminoethoxy)ethanol, triethylene glycol monoamine, α-(2-hydroxymethylethyl)-ω-(2-aminomethylethoxy)poly(oxy(methyl-1,2-ethanediyl)), 3-(2-hydroxyethoxy)propylamine, 3-(2-(2-hydroxyethoxy)ethoxy)propylamine, 3-(6-hydroxyhexyloxy) propylamine, 6-amino-1-hexanethiol, 8-amino-1-octanethiol, 10-amino-1-decanethiol and 12-amino-1-dodecanethiol.

Preferred amines B are di- or polyfunctional aliphatic amines which, in addition to one or more primary amino groups, carry a secondary amino group, in particular N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethylpiperidine, 3-(4-aminobutyl)piperidine, DETA, DPTA, BHMT and fatty diamines, such as N-cocoalkyl-1,3-propanediamine, N-oleyl-1,3-propanediamine, N-soyaalkyl-1,3-propanediamine and N-tallowalkyl-1,3-propanediamine. Aliphatic hydroxy- and mercaptoamines in which the primary amino group are separated from the hydroxyl or the mercapto group by a chain of at least 5 atoms or by a ring are also preferred, in particular 5-amino-1-pentanol, 6-amino-1-hexanol and higher homologues thereof, 4-(2-aminoethyl)-2-hydroxyethylbenzene, 3-aminomethyl-3,5,5-trimethylcyclohexanol, 2-(2-aminoethoxy)ethanol, triethylene glycol monoamine and higher oligomers and polymers thereof, 3-(2-hydroxyethoxy)propylamine, 3-(2-(2-hydroxyethoxy)ethoxy)propylamine and 3-(6-hydroxyhexyloxy)propylamine.

The reaction between an aldehyde A and an amine B leads to hydroxyaldimines if the amine B used is a hydroxyamine; to mercaptoaldimines if the amine B used is a mercaptoamine; to aminoaldimines if the amine B used is a di- or polyfunctional amine which, in addition to one or more primary amino groups, carries one or more secondary amino groups; or to ureaaldimines if the amine B used is a trisubstituted urea which carries one or more primary amino groups.

In one embodiment, the aldimines of the formula (XI) have a substituent $N—R^8$ as substituent X. Such aldimines of the formula (XI) can be prepared by reacting at least one sterically hindered aliphatic aldehyde A of the formula (IV) with at least one di- or polyfunctional aliphatic primary amine C of the formula $[H_2N]_m—R^4—NH_2$ in a first step to give an intermediate of the formula (VII) which, in addition to one or more aldimino groups, also contains a primary amino group, and then reacting this intermediate in a second step in an addition reaction with a Michael acceptor of the formula (VIII) in a ratio of the number of double bonds:number of $NH_2$ groups=1:1. An aminoaldimine which, in addition to one or more aldimino groups, also contains at least one, preferably precisely one, secondary amino group forms thereby.

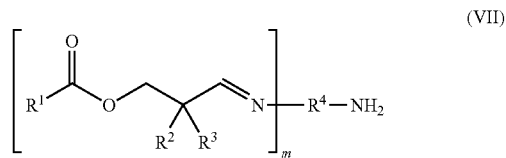

(VII)

In the formula (VII), m, $R^1$, $R^2$, $R^3$ and $R^4$ have the same meaning as described for formula (I).

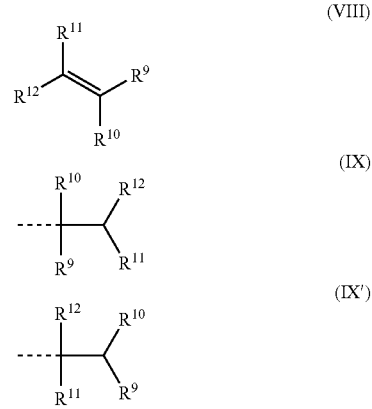

(VIII)

(IX)

(IX')

Thus, aldimines of the formula (XI) form in which X is the radicals N—$R^8$ and $R^8$ is a monovalent hydrocarbon radical of the formula (IX) or (IX'). In the formulae (VIII), (IX) and (IX'), $R^9$ is a radical which is selected from the group consisting of —$COOR^{13}$, —CN, —$NO_2$, —$PO(OR^{13})_2$, —$SO_2R^{13}$ and —$SO_2OR^{13}$ and $R^{10}$ is a hydrogen atom or a radical from the group consisting of —$R^{13}$, —$COOR^{13}$ and —$CH_2COOR^{13}$ and $R^{11}$ and $R^{12}$, independently of one another, are a hydrogen atom or a radical from the group consisting of —$R^{13}$, —$COOR^{13}$ and —CN, $R^{13}$ being a monovalent hydrocarbon radical having 1 to 20 C atoms.

The amine C is an aliphatic amine having at least two primary amino groups.

Examples of suitable amines C are aliphatic polyamines, such as ethylenediamine, 1,2- and 1,3-propanediamine, 2-methyl-1,2-propanediamine, 2,2-dimethyl-1,3-propanediamine, 1,3- and 1,4-butanediamine, 1,3- and 1,5-pentanediamine, 2-butyl-2-ethyl-1,5-pentanediamine, 1,6-hexamethylenediamine (HMDA), 2,2,4- and 2,4,4-trimethylhexamethylenediamine and mixtures thereof (TMD), 1,7-heptanediamine, 1,8-octanediamine, 2,4-dimethyl-1,8-octanediamine, 4-aminomethyl-1,8-octanediamine, 1,9-nonanediamine, 2-methyl-1,9-nonanediamine, 5-methyl-1,9-nonanediamine, 1,10-decanediamine, isodecanediamine, 1,11-undecanediamine, 1,12-dodecanediamine, methylbis(3-aminopropyl)amine, 1,5-diamino-2-methylpentane (MPMD), 1,3-diaminopentane (DAMP), 2,5-dimethyl-1,6-hexamethylenediamine, cycloaliphatic polyamines, such as 1,2-, 1,3- and 1,4-diaminocyclohexane, bis(4-aminocyclohexyl)methane ($H_{12}$MDA), bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane (M-MECA), 1-amino-3-aminomethyl-3,5,5-trimethylcyclohexane (=isophoronediamine or IPDA), 2- and 4-methyl-1,3-diaminocyclohexane and mixtures thereof, 1,3- and 1,4-bis(aminomethyl)cyclohexane, 1,3,5-tris(aminomethyl)cyclohexane, 1-cyclohexylamino-3-aminopropane, 2,5(2,6)-bis(aminomethyl)bicyclo[2.2.1]heptane (NBDA, produced by Mitsui Chemicals), 3(4),8(9)-bis(aminomethyl)tricyclo-[5.2.1.0$^{2,6}$]decane, 1,4-diamino-2,2,6-trimethylcyclohexane (TMCDA), 3,9-bis(3-aminopropyl)-2,4,8,10-tetraoxaspiro[5.5]undecane, arylaliphatic polyamines, such as 1,3-xylylenediamine (MXDA), 1,4-xylylenediamine (PXDA), 1,3,5-tris(aminomethyl)benzene, aliphatic polyamines containing ether groups, such as bis(2-aminoethyl)ether, 4,7-dioxadecane-1,10-diamine, 4,9-dioxadodecane-1,12-diamine and higher oligomers thereof, polyoxyalkylenepolyamines having theoretically two or three amino groups, obtainable, for example, under the name Jeffamine® (produced by Huntsman Chemicals). Di- or triamines in which the primary amino groups are separated by a chain of at least 5 atoms or by a ring are preferred, in particular 1,5-diamino-2-methylpentane, 1,6-hexamethylenediamine, 2,2,4- and 2,4,4-trimethylhexamethylenediamine and mixtures thereof, 1,10-decanediamine, 1,12-dodecanediamine, 1,3- and 1,4-diaminocyclohexane, bis(4-aminocyclohexyl)methane, bis(4-amino-3-methylcyclohexyl)methane, 1-amino-3-aminomethyl-3,5,5-trimethylcyclohexane, 1,3- and 1,4-bis(aminomethyl)cyclohexane, 2,5(2,6)-bis(aminomethyl)bicyclo[2.2.1]heptane, 3(4),8(9)-bis(aminomethyl)tricyclo[5.2.1.0$^{2,6}$]decane, 1,4-diamino-2,2,6-trimethylcyclohexane (TMCDA), 3,9-bis(3-aminopropyl)-2,4,8,10-tetraoxaspiro[5.5]undecane, 1,3- and 1,4-xylylenediamine, 1,3,5-tris(aminomethyl)benzene, and polyoxyalkylenepolyamines having theoretically two or three amino groups, obtainable, for example, under the name Jeffamine® (produced by Huntsman Chemicals).

Examples of suitable Michael acceptors of the formula (VIII) are maleic or fumaric acid diesters, such as dimethyl maleate, diethyl maleate, dibutyl maleate, diethyl fumarate; citraconic acid diesters, such as dimethyl citraconate; acrylic or methacrylic acid esters, such as methyl (meth)acrylate, ethyl (meth)acrylate, butyl (meth)acrylate, lauryl (meth)acrylate, stearyl (meth)acrylate, tetrahydrofuryl (meth)acrylate, isobornyl (meth)acrylate; itaconic acid diesters, such as dimethyl itaconate; cinnamic acid esters, such as methyl cinnamate; vinylphosphonic acid diesters, such as dimethyl vinylphosphonate; vinylsulfonic acid esters, in particular aryl vinylsulfonates; vinylsulfones; vinylnitriles, such as acrylonitrile, 2-pentenenitrile or fumaronitrile; 1-nitroethylenes, such as β-nitrostyrene; and Knoevenagel condensates, such as, for example, those from malonic acid diesters and aldehydes, such as formaldehyde, acetaldehyde or benzaldehyde. Maleic acid diesters, acrylic acid esters, phosphonic acid diesters and vinylnitriles are preferred.

The reaction of the aldehyde A with the amine C to give the intermediate of the formula (VII) takes place in a condensation reaction with elimination of water, as described further above for the reaction of the aldehyde A with the amine B. The stoichiometry between the aldehyde A and the amine C is chosen so that m mol of aldehyde A are used for 1 mol of amine C which contains m+1 primary amino groups. A solvent-free preparation process is preferred, the water formed in the condensation being removed from the reaction mixture by application of a vacuum.

The reaction of the intermediate of the formula (VII) with the Michael acceptor of the formula (VIII) is effected, for example, by mixing the intermediate with a stoichiometric or slightly superstoichiometric amount of the Michael acceptor of the formula (VIII) and heating the mixture at temperatures of from 20 to 110° C. until complete conversion of the intermediate into the aldimine of the formula (XI). The reaction preferably takes place without the use of solvents.

The aldimines of the formula (XI) may be in equilibrium with cyclic forms, as shown by way of example in formula (X). These cyclic forms are cyclic aminals, for example imidazolidines or tetrahydropyrimidines, in the case of aminoaldimines; cyclic aminoacetals, for example oxazolidines or tetrahydrooxazines, in the case of hydroxyaldimines; cyclic thioaminals, for example thiazolidines or tetrahydrothiazines, in the case of mercaptoaldimines.

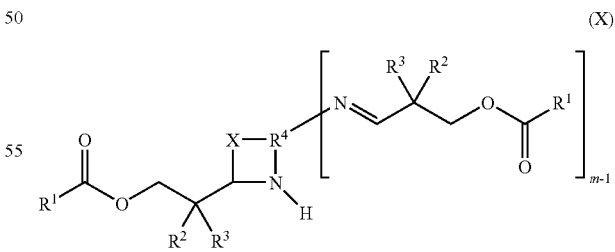

(X)

In the formula (X), m, $R^1$, $R^2$, $R^3$, $R^4$ and X have the same meaning as described for formula (I).

Surprisingly, most aldimines of the formula (XI) do not tend to cyclization. Particularly from aminoaldimines, it is possible by means of IR and NMR spectroscopic methods to show that these compounds are present predominantly in the open-chain, i.e. the aldimine, form, whereas the cyclic, i.e. the aminal, form does not occur or occurs only in traces. This is contrary to the behavior of the aminoaldimines according to the prior art, as described, for example, in U.S. Pat. No. 4,404,379 and U.S. Pat. No. 6,136,942: these are in fact present mainly in cycloaminal form. Hydroxy- and mercaptoamines in which the primary amino group are separated from the hydroxyl or the mercapto group by a chain of at least 5 atoms or by a ring also show scarcely any cyclization. The substantial absence of cyclic structures in the aldimines of the formula (XI) is to be regarded as an advantage, particularly with regard to the use thereof in isocyanate-containing compositions, since the aldimines are thus substantially free of the basic nitrogen atoms which occur in aminals, oxazolidines and thioaminals and which might reduce the shelf-life of the isocyanate-containing composition.

The aldimines of the formula (XI) are odorless. They have a long shelf-life under suitable conditions, in particular in the absence of moisture. On admission of moisture, the aldimino groups of the aldimines may hydrolyze via intermediates formally to amino groups, the corresponding aldehyde A used for the preparation of the aldimine being liberated. Since this hydrolysis reaction is reversible and the chemical equilibrium lies substantially on the aldimine side, it is to be assumed that, in the absence of groups reactive toward amines, only some of the aldimino groups undergo partial or complete hydrolysis.

Suitable compounds D are substances which carry more than one of the following reactive groups which can undergo addition reactions: isocyanate, isothiocyanate, cyclocarbonate, epoxide, episulfide, aziridine, acrylate, methacrylate, 1-ethynylcarbonyl, 1-propynylcarbonyl, maleimide, citraconimide, vinyl, isopropenyl and allyl groups, and compounds having different reactive groups from among the abovementioned ones. Isocyanate, epoxide, acrylate, maleimide, vinyl, isopropenyl and allyl groups are preferred. The isocyanate group is particularly preferred.

Compounds D are, in particular, compounds of the formula (XII)

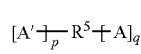

in which A' is a reactive group which is selected from the group consisting of

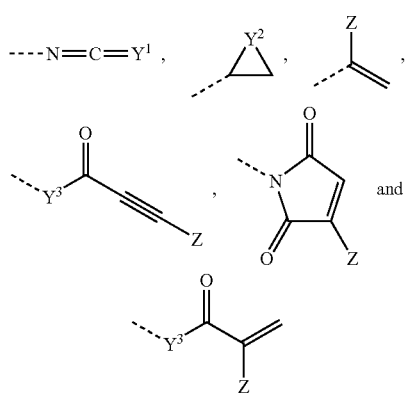

and in which A' may be identical to the reactive group A or different therefrom and the other substituents and indices are as described for formula (I).

Examples of suitable compounds D are
di- or polyfunctional, monomeric and/or oligomeric aliphatic, cycloaliphatic, arylaliphatic and aromatic isocyanates (polyisocyanates), such as 1,6-hexamethylene diisocyanate (HDI), 2-methylpentamethylene 1,5-diisocyanate, 2,2,4- and 2,4,4-trimethylhexamethylene 1,6-diisocyanate (TMDI), 1,12-dodecamethylene diisocyanate, lysine and lysine ester diisocyanate, cyclohexane 1,3- and 1,4-diisocyanate and any desired mixtures of these isomers, 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), 1,3,5-tris(isocyanatomethyl)benzene, m- and p-tetramethylxylene 1,3- and 1,4-diisocyanate (m- and p-TMXDI), bis(1-isocyanato-1-methylethyl)naphthalene, α,α,α',α',α'',α''-hexamethylmesitylene 1,3,5-triisocyanate, dimer and trimer fatty acid isocyanates, such as 3,6-bis(9-isocyanatononyl)-4,5-di(1-heptenyl) cyclohexene (dimeryl diisocyanate), 2,4- and 2,6-toluoylene diisocyanate and any desired mixtures of these isomers (TDI), 4,4'-, 2,4'- and 2,2'-diphenylmethane diisocyanate and any desired mixtures of these isomers (MDI), mixtures of MDI and MDI homologues (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatobiphenyl (TOBI), tris(4-isocyanatophenyl) methane, tris(4-isocyanatophenyl) thiophosphate; oligomers of these isocyanates containing uretdione, isocyanurate or iminooxadiazinedione groups; modified difunctional and polyfunctional isocyanates containing esters, urea, urethane, biuret, allophanate, carbodiimide, uretonimine or oxadiazinetrione groups; and isocyanate-containing polyurethane polymers, i.e. reaction products of polyisocyanates with substances having two or more hydroxyl groups (so-called "polyols"), which reaction products have more than one isocyanate group, such as, for example, dihydric or polyhydric alcohols, glycols or aminoalcohols, polyhydroxyfunctional polyethers, polyesters, polyacrylates, polycarbonates or polyhydrocarbons, in particular polyethers;
di- or polyfunctional epoxides (polyepoxides), such as bis (2,3-epoxycyclopentyl)ether, polyglycidyl ethers of polyhydric aliphatic and cycloaliphatic alcohols, such as 1,4-butanediol, polypropylene glycols and 2,2-bis(4-hydroxycyclohexyl)propane; polyglycidyl ethers of polyhydric phenols, such as resorcinol, bis(4-hydroxyphenyl)methane (bisphenol F), 2,2-bis(4-hydroxyphenyl) propane (bisphenol A), 2,2-bis(4-hydroxy-3,5-dibromophenyl)propane, 1,1,2,2-tetrakis(4-hydroxyphenyl)ethane, condensates of phenols with formaldehyde which are obtained under acidic conditions, such as phenol novolaks and cresol novolaks, and polyglycidyl ethers pre-extended with these alcohols and phenols or with polycarboxylic acids, such as, for example, dimeric fatty acids, or a mixture thereof; polyglycidyl esters of polybasic carboxylic acids, such as phthalic acid, terephthalic acid, tetrahydrophthalic acid and hexahydrophthalic acid; N-glycidyl derivatives of amines, amides and heterocyclic nitrogen bases, such as N,N-diglycidylaniline, N,N-diglycidyltoluidine, N,N,O-triglycidyl-4-aminophenol, N,N,N',N'-tetraglycidylbis(4-aminophenyl)methane, triglycidyl cyanurate and triglycidyl isocyanurate;

difunctional or polyfunctional compounds carrying acrylate, methacrylate or acrylamido groups, such as tris(2-hydroxyethyl)isocyanurate tri(meth)acrylate, tris(2-hydroxyethyl)cyanurate tri(meth)acrylate, N,N',N''-tris (meth)acryloylperhydrotriazine; di- or polyfunctional acrylates and methacrylates of aliphatic polyethers, polyesters, novolaks, phenols, aliphatic or cycloaliphatic alcohols, glycols and polyester glycols and mono- and polyalkoxylated derivatives of the abovementioned compounds, for example ethylene glycol di(meth)acrylate, tetraethylene glycol di(meth)acrylate, tripropylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, trimethylolpropane tri(meth)acrylate, pentaerythritol tetra(meth)acrylate, dipentaerythritol tetra(meth)acrylate, dipentaerythritol penta(meth)acrylate, dipentaerythritol hexa(meth)acrylate; acrylate- or methacrylate-functional polybutadienes, polyisoprenes or block copolymers thereof having a functionality of two or more; adducts of difunctional or polyfunctional epoxides, such as the above-mentioned epoxides, with acrylic and methacrylic acid; difunctional or polyfunctional polyurethane (meth)acrylates; difunctional or polyfunctional acrylamides, such as N,N'-methylenebisacrylamide;

difunctional or polyfunctional compounds carrying 1-ethynylcarbonyl or 1-propynylcarbonyl groups;

difunctional or polyfunctional compounds carrying maleimide or citraconimide groups, such as the bis- and polykismaleimides from aliphatic, cycloaliphatic or aromatic di- and polyamines and maleic or citraconic anhydride, for example α,ω-dimer fatty acid bis(maleimide), 4,4'-diphenylmethanebis(maleimide), 1,3-xylylenebis (citraconimide); bis- and polykismaleimides from amino-terminated butadiene/acrylonitrile copolymers (for example obtainable under the name Hycar® ATBN from Noveon) and maleic or citraconic anhydride; difunctional or polyfunctional adducts of di- and polyisocyanates with N-hydroxyethylmaleimide; esters of dihydric or polyhydric alcohols and 6-maleimidohexanoic acid;

di- or polyfunctional compounds carrying vinyl and/or isopropenyl groups, such as 1,3- and 1,4-divinylbenzene, divinyl sulfone, vinyl crotonate, diallylidenepentaerythritol acetal, 1,3-diisopropenylbenzene and 1,3,5-triisopropenylbenzene, 3-(2-vinyloxyethoxy)styrene, divinyldimethylsilane, trivinylmethylsilane, trivinylmethoxysilane, divinyltetramethyldisiloxane, 1,3-divinyl-1,3-diphenyl-1,3-dimethyldisiloxane, 1,3-divinyltetraethoxydisiloxane, trivinylpentamethyltrisiloxane, 4-vinyloxybutoxytrivinylsilane, tris(4-vinyloxybutoxy)vinylsilane; di- or polyfunctional vinyl and isopropenyl ethers, such as divinyl ether, isopropenyl vinyl ether, triethylene glycol divinyl ether, butanediol divinyl ether, hexanediol divinyl ether, octadecanediol divinyl ether, dimer fatty acid diol divinyl ether and divinylbutyral; divinyl esters of dicarboxylic acids, for example divinyl adipate;

di- or polyfunctional compounds carrying allyl groups, such as triallyl cyanurate, triallyl isocyanurate, triallyl phosphate; di- or polyfunctional allyl ethers of alcohols and glycols and mono- and polyalkoxylated derivatives thereof, for example 1,4-bis(allyloxy)butane, 1,6-bis(allyloxy)hexane, triethylene glycol diallyl ether, bisphenol A diallyl ether, 3,3'-diallylbisphenol A diallyl ether, 3,3'-diallylbisphenol A, trimethylolpropane diallyl ether, glyceryl triallyl ether, trimethylolpropane triallyl ether, pentaerythritol tetraallyl ether; di- or polyfunctional allyl esters and allylamides of carboxylic acids, for example diallyl phthalate, diallyl isophthalate and terephthalate, diallyl oxalate, diallyl sebacate, diallyl maleate, diallyl fumarate, diallyl itaconate; difunctional allyl carbonates, such as diallyl carbonate, di- and triethylene glycol bisallyl carbonate; difunctional or polyfunctional adducts of di- and polyisocyanates with glycidol, allyl alcohol or allyl glycols, for example 1,6-hexamethylenebisallyl carbamate;

and di- or polyfunctional compounds which are heterofunctional, i.e. carry at least two different reactive groups from among the abovementioned ones, (A different from A') such as 4-allyloxyphenyl isocyanate, 1-alkenyl isocyanates, such as vinyl isocyanate, propenyl isocyanate and isopropenyl isocyanate, 2-isocyanatoethyl methacrylate, 1,2-dimethyl-3-isocyanatopropyl acrylate, p-isocyanatostyrene, m- and p-isopropenyl-α,α-dimethylbenzyl isocyanate (m- and p-TMI), m- and p-ethenyl-α,α-dimethylbenzyl isocyanate, isopropenyl-α,α,α',α'-tetramethylxylylene diisocyanate, glycidyl allyl ether, glycidyloxytrivinylsilane, triglycidyloxyvinylsilane, N-(trivinylsilyloxymethyl)maleimide; heterofunctional adducts of di- and polyisocyanates with glycidol, allyl alcohol, allyl glycols, N-hydroxyethylmaleimide, hydroxyfunctional acrylates and methacrylates, such as 2-hydroxyethyl acrylate and methacrylate; heterofunctional adducts of mono- and polycarbodiimides of di- and polyisocyanates with acrylic or methacrylic acid; heterofunctional adducts of di- or polyfunctional epoxides with acrylic or methacrylic acid, vinyl allyl ether, ethylene glycol vinyl allyl ether, vinyl allyl phthalate, ethylene glycol 2-allylphenyl vinyl ether, allyl (meth)acrylate, vinyl acrylate, 2-vinyloxyethyl (meth)acrylate.

Particularly suitable compounds D are di- or polyfunctional aliphatic, cycloaliphatic, arylaliphatic and aromatic isocyanates, such as the monomeric and oligomeric polyisocyanates mentioned and the reaction products of polyisocyanates with polyols, in particular polyether polyols, polyester polyols, polyacrylate polyols, polycarbonate polyols, polyhydrocarbon polyols and mixtures of these polyols, which reaction products have more than one isocyanate group.

Depending on the reactive groups of the compound D and that group of the aldimine of the formula (XI) which carries the active hydrogen, the addition reaction may be nucleophilic or free radical. For reasons of simplicity, the term "addition reaction" in the present document is also to comprise ring-opening substitution reactions as undergone by, for example, epoxides with nucleophiles, because the result of such a substitution reaction not liberating the nucleofuge as a separate molecule is equivalent to an addition reaction. The addition reaction is nucleophilic if that reactive group of the aldimine which carries the active hydrogen acts as a nucleophile by attacking an electrophilic reactive group of the compound D, for example in the case of the attack of an amino or hydroxyl group at an isocyanate group. The reaction of a mercapto group at an acrylate group may be mentioned as an example of a free radical addition reaction, a free radical initiator generally being required for this type of addition reaction.

The reaction between the aldimine of the formula (XI) and the compound D to give the adduct i.e. an aldimine-containing compound of the formula (I), takes place under known conditions as are typically used for reactions between the reactive groups participating in the respective reaction, for example at from 20 to 100° C. The reaction takes place with the use of a solvent or preferably in the absence of a solvent. If appropriate, auxiliaries, such as, for example, catalysts, initiators or stabilizers, can be concomitantly used. The reaction with isocyanates is preferably carried out at room temperature and without a catalyst for aminoaldimines, and at from 40 to 100° C. and with the use of a catalyst as is used for the urethanization reaction between isocyanates and alcohols, for example an organotin compound, a bismuth complex, a tertiary amine compound or a combination of such catalysts, for hydroxy-, mercapto- and ureaaldimines.

If the reaction is carried out stoichiometrically, i.e. with one mole equivalent of active hydrogen of the aldimine per mole equivalent of reactive groups of the compound D—with the result that the reactive groups thereof are completely reacted—a polyaldimine is obtained as adduct. Thus, diverse polyaldimines are obtained in a simple manner without having had to rely for their preparation on the corresponding primary polyamines, which are technically and commercially available only to a limited extent. Depending on structure, functionality and molecular weight of the compounds D and of the aldimines of the formula (XI), these polyaldimines may have very different properties; they can therefore be tailored to the needs of a certain application.

By suitable reaction of the aldimines of the formula (XI) with compounds D, it is also possible to prepare aldimine-containing compounds of the formula (I) which are heterofunctional, i.e. which, in addition to one or more aldimino groups, also have one or more other reactive groups accessible to polyreactions. Heterofunctional aldimine-containing compounds of the formula (I) are obtained when the reaction between the aldimine of the formula (XI) and a compound D is carried out substoichiometrically, i.e. with less than one mole equivalent of active hydrogen of the aldimine per mole equivalent of reactive groups of the compound D. The compound D itself may be homo- or heterofunctional.

The adducts of aldimines of the formula (XI) with compounds D obtained in the manner described, i.e. aldimine-containing compounds of the formula (I), are, like the aldimines of the formula (XI), odorless. They have a long shelf-life under suitable conditions, in particular in the absence of moisture. Heterofunctional adducts which, in addition to aldimino groups, contain additional reactive groups accessible to polyreactions have a long shelf-life when they are moreover kept away from factors triggering reactions of these reactive groups, such as, for example, heat or UV radiation.

The aldimines of the formula (XI) and the aldimine-containing compounds of the formula (I) can be very widely used. In principle, they can be used wherever they can serve as a source of the aldehydes of the formula (IV) and/or of the amines B. In particular, they can be used in the function of protected amines or protected aldehydes, in aldehyde- and/or amine-reactive systems, and can be deprotected there in a targeted manner if required. In particular, they are used in systems in which compounds which react with primary amines are present. The deprotection is effected hydrolytically, for example by contact with water or moisture, in particular atmospheric humidity.

On admission of moisture, the aldimino groups of the aldimines of the formula (XI), and the aldimine-containing compounds of the formula (I) can hydrolyze via intermediates formally to amino groups, the corresponding aldehyde A used for the preparation of the aldimine of the formula (XI) being liberated. Since this hydrolysis reaction is reversible and the chemical equilibrium is substantially on the aldimine side, it is to be assumed that, in the absence of groups reactive toward amines, only some of the aldimino groups undergo partial or complete hydrolysis. In the special case of heterofunctional adducts, which contain groups reactive toward amines, in particular isocyanate groups, the hydrolyzing aldimino groups on the other hand react further, for example with isocyanate groups to give urea groups. In these cases, where in formula (I) the values of m, p and q are selected such that m·p≦q, there is crosslinking of the heterofunctional adduct, which may also lead directly to a high molecular weight plastic without participation of further substances. The reaction of the groups reactive toward amines with the hydrolyzing aldimino groups need not necessarily take place via amino groups. Of course, reactions with intermediates of the hydrolysis reaction are also possible. For example, it is conceivable that the hydrolyzing aldimino group in the form of a hemiaminal will react directly with the groups reactive toward amines.

Suitable catalysts for the hydrolysis of the aldimino groups are, for example, organic carboxylic acids, such as benzoic acid, salicylic acid or 2-nitrobenzoic acid, organic carboxylic anhydrides, such as phthalic anhydride or hexahydrophthalic anhydride, silyl esters of organic carboxylic acids, organic sulfonic acids, such as methanesulfonic acid, p-toluene-sulfonic acid or 4-dodecylbenzenesulfonic acid, or other organic or inorganic acids or mixtures of the above-mentioned acids.

The aldimine-containing compounds of the formula (I) can be used, for example, as building blocks for plastic precursors. In the present document, the term "plastic precursors" designates monomeric, oligomeric or polymeric organic compounds—or homogeneous or heterogeneous compositions substantially containing such compounds—which, owing to reactive groups present in them and accessible to polyreactions, are capable, alone or together with other molecules, of reacting to give high molecular weight plastics, i.e. organic polymers, a process which is generally designated as "curing" or as "crosslinking"—independently of whether the reactions taking place during the curing lead to covalently or otherwise crosslinked structures. The term "polyreactions" comprises all types of polyaddition, polycondensation and polymerization reactions. In the present document, the term "polymer" comprises both a group of macromolecules which are chemically uniform but differ with respect to degree of polymerization, molar mass and chain length and which were prepared by a polyreaction and derivatives of such a group of macromolecules from polyreactions, i.e. compounds which were obtained by reactions such as, for example, additions or substitutions, of functional groups with specified macromolecules which may be chemically uniform or chemically non-uniform. The prefix "poly" in substance designations, such as "polyaldimine", "polyamine", "polyisocyanate" or "polyol" indicates in the present document that the respective substance formally contains more than one of the functional group occurring in its designation per molecule.

Purely aldimino-functional compounds of the formula (I) which represent polyaldimine can be used as building blocks, in particular as latent curing agents, for plastic precursors which contain reactive groups which are reactive toward aldimino groups as such or hydrolyzed forms thereof. Heterofunctional compounds of the formula (I) which, in addition to the aldimino groups, also contain at least one further reactive group accessible to polyreactions can be used as building blocks, for example as comonomers or latent curing agents, for plastic precursors; or, if the aldimino group as such or after its hydrolysis can react with the other reactive groups present in the compound of the formula (I) with linkage of the molecules, also as plastic precursors themselves. This applies in particular to the case of aldimine-containing compounds of the formula (I) which additionally contain isocyanate groups.

Suitable plastic precursors in which the aldimine-containing compounds of the formula (I) described can be used as building blocks, for example as latent curing agents or as comonomers, are those which contain substances having at least one type of reactive groups which undergo reactions with aldimines as such or after the partial or complete hydrolysis thereof, which reactions by themselves or in combination with further reactions lead to crosslinking of the plastic precursor. Examples of such reactive groups are isocyanate, isothiocyanate, epoxide, episulfide and cyclocarbonate groups. The reactions of these reactive groups with the aldimino groups can be initiated by moisture and/or by heat. Particularly suitable reactive groups are isocyanate groups, isothiocyanate groups and epoxide groups. Suitable plastic precursors are also those plastic precursors which, in addition to the substances having said reactive groups, contain further substances having groups accessible to polyreactions, such as, for example, aziridine, acrylate, methacrylate, 1-ethynyl-carbonyl, 1-propynylcarbonyl, maleimide, citraconimide, vinyl, isopropenyl, allyl or silanol groups, or groups which hydrolyze to give silanol groups.

Suitable plastic precursors for which the aldimine-containing compounds of the formula (I) can be used as building blocks, for example as latent curing agents or as comonomers, are those which contain at least one type of the abovementioned reactive groups, in particular isocyanate groups, isothiocyanate groups and epoxide groups. Other suitable plastic precursors are heterofunctional plastic precursors, i.e. plastic precursors which contain two or more different types of reactive groups accessible to polyreactions, such as isocyanate, isothiocyanate, epoxide, episulfide, cyclocarbonate, aziridine, acryloyl, methacryloyl, 1-ethynylcarbonyl, 1-propynylcarbonyl, maleimide, citraconimide, vinyl, isopropenyl, allyl or silanol groups, or groups which hydrolyze to give silanol groups.

Particularly suitable plastic precursors in which the aldimine-containing compounds of the formula (I) can be used are isocyanate-containing compositions, i.e. those plastic precursors which contain as reactive groups exclusively or to a substantial extent isocyanate groups which are part of polyurethane polymers and/or of polyisocyanates.

Suitable plastic precursors which contain the aldimine-containing compounds of the formula (I) as constituents may be one-component or two-component ones.

Particularly suitable one-component plastic precursors are one-component isocyanate-containing compositions which contain at least one aldimine-containing compound of the formula (I) and at least one isocyanate-containing polyurethane polymer P which is a reaction product of polyisocyanates and polyols. In the present document, the term "polyurethane polymer" comprises all polymers which are prepared by the diisocyanate polyaddition method. This also includes those polymers which are virtually or completely free of urethane groups, such as polyether polyurethanes, polyester polyurethanes, polyether polyureas, polyureas, polyester polyureas, polyisocyanurates, polycarbodiimides, etc.

The isocyanate-containing polyurethane polymer P is prepared by reacting at least one polyol with at least one polyisocyanate. This reaction can be effected by reacting the polyol and the polyisocyanate by customary methods, for example at temperatures of from 50° C. to 100° C., optionally with the concomitant use of suitable catalysts, the polyisocyanate being metered so that the isocyanate groups thereof are present in stoichiometric excess relative to the hydroxyl groups of the polyol. The excess of polyisocyanate is chosen so that, for example, a content of free isocyanate groups of 0.1-15% by weight, in particular 0.5-5% by weight, based on the total polyurethane polymer P, remains in the resulting polyurethane polymer P after the reaction of all hydroxyl groups of the polyol. If appropriate, the polyurethane polymer P can be prepared with the concomitant use of plasticizers, the plasticizers used containing no groups reactive toward isocyanates.

The following commercially available polyols or any desired mixtures thereof can, for example, be used as polyols for the preparation of such an isocyanate-containing polyurethane polymer P:

polyoxyalkylene polyols, also referred to as polyether polyols or oligoetherols, which are polymerization products of ethylene oxide, 1,2-propylene oxide, 1,2- or 2,3-butylene oxide, tetrahydrofuran or mixtures thereof, possibly polymerized with the aid of an initiator having two or more active hydrogen atoms per molecule, such as, for example, water, ammonia or compounds having a plurality of OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline and mixtures of the abovementioned compounds. Both polyoxyalkylene polyols which have a low degree of unsaturation (measured according to ASTM D-2849-69 and stated in milliequivalent of unsaturation per gram of polyol (mEq/g)), prepared, for example, with the aid of so-called double metal cyanide complex catalysts (DMC catalysts), and polyoxyalkylene polyols having a higher degree of unsaturation, prepared, for example, with the aid of anionic catalysts, such as NaOH, KOH, CsOH or alkali metal alcoholates, can be used.

Polyoxyalkylenediols or polyoxyalkylenetriols, in particular polyoxypropylenediols or polyoxypropylenetriols, are particularly suitable.

Polyoxyalkylenediols or polyoxyalkylenetriols having a degree of unsaturation of less than 0.02 mEq/g and having a molecular weight in the range of 1000-30 000 g/mol and polyoxypropylenediols and -triols having a molecular weight of 400-8000 g/mol are especially suitable. In the present document, the term "molecular weight" designates the average molecular weight $M_n$.

Also particularly suitable are so-called ethylene oxide-terminated ("EO-endcapped", ethylene oxide-endcapped) polyoxypropylene polyols. The latter are special polyoxypropylenepolyoxyethylene polyols which are obtained, for example, if pure polyoxypropylene polyols, in particular polyoxypropylenediols and -triols, are further alkoxylated with ethylene oxide after the end of the polypropoxylation reaction and thus have primary hydroxyl groups.

Styrene/acrylonitrile and acrylonitrile/methyl methacrylate-grafted polyether polyols.

Polyester polyols, also referred to as oligoesterols, prepared, for example, from dihydric or trihydric alcohols, such as, for example, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the abovementioned alcohols, with organic dicarboxylic acids or the anhydrides or esters thereof, such as, for example, succinic acid, glutaric acid, adipic acid, suberic acid, sebacic acid, dodecanedicarboxylic acid, maleic acid, fumaric acid, phthalic acid, isophthalic acid, terephthalic acid and hexahydrophthalic acid or mixtures of the abovementioned acids, and polyester polyols from lactones, such as, for example, ε-caprolactone.

Polycarbonate polyols as are obtainable by reacting, for example, the abovementioned alcohols—used for the synthesis of the polyester polyols—with dialkyl carbonates, diaryl carbonates or phosgene.

Polyacrylate- and polymethacrylate polyols.

Polyhydrocarbon polyols, also referred to a oligohydrocarbonols, such as, for example, polyhydroxyfunctional ethylene/propylene, ethylene/butylene or ethylene/propylene/diene copolymers, as are produced, for example, by Kraton Polymers or polyhydroxyfunctional copolymers from dienes, such as 1,3-butadiene or diene mixtures, and vinyl monomers, such as styrene, acrylonitrile or isobutylene, or polyhydroxyfunctional polybutadiene polyols, such as, for example, those which are prepared by copolymerization of 1,3-butadiene and allyl alcohol.

Polyhydroxyfunctional acrylonitrile/polybutadiene copolymers, as can be prepared, for example, from epoxides or amino alcohols and carboxyl-terminated acrylonitrile/polybutadiene copolymers (commercially available under the name Hycar® CTBN from Hanse Chemie).

These stated polyols have an average molecular weight of 250-30 000 g/mol, in particular of 1000-30 000 g/mol, and an average OH functionality in the range from 1.6 to 3.

In addition to these stated polyols, small amounts of low molecular weight di- or polyhydric alcohols, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, 1,1,1-trimethylolethane, 1,1,1-trimethylolpropane, glycerol, pentaerythritol, sugar alcohols, such as xylitol, sorbitol or mannitol, sugars, such as sucrose, other higher-hydric alcohols, low molecular weight alkoxylation products of the abovementioned di- and polyhydric alcohols, and mixtures of the abovementioned alcohols can be concomitantly used in the preparation of the polyurethane polymer P.

The mono- or oligomeric di- or polyfunctional isocyanates, such as those which were mentioned as being suitable as compounds D, are used as polyisocyanates for the preparation of such an isocyanate-containing polyurethane polymer. Particularly suitable polyisocyanates are MDI, HDI, TDI and IPDI.

The one-component plastic precursor contains at least one aldimine-containing compound of the formula (I), in particular in one of the preferred embodiments already described in detail above. The aldimine-containing compound of the formula (I) can be prepared separately and incorporated as such into the plastic precursor. However, it can also be prepared in situ, i.e. in the course of the preparation of the plastic precursor, by reacting suitable amounts of at least one aldimine of the formula (XI) and at least one compound D in situ, i.e. in the presence of further constituents of the plastic precursor, to give the adduct. In particular, the one-component isocyanate-containing compositions described can be prepared by a procedure in which suitable amounts of at least one aldimine of the formula (XI) and at least one compound D are reacted in situ, the compound D preferably being an isocyanate-containing polyurethane polymer as described above in detail as polyurethane polymer P.

The one-component isocyanate-containing composition contains at least one aldimine-containing compound of the formula (I) or a preferred embodiment thereof, as has been described above in detail. The aldimine-containing compound of the formula (I) can be prepared separately and mixed with the isocyanate-containing polyurethane polymer P. However, it can also be prepared in situ, i.e. in the course of the preparation of the isocyanate-containing composition, by mixing at least one aldimine of the formula (XI) with at least one isocyanate-containing polyurethane polymer P in a suitable stoichiometric ratio and reacting them thereby to give the adduct.

The aldimine-containing compound of the formula (I) is typically present in an amount of from 0.1 to 30% by weight, preferably from 0.5 to 20% by weight and in particular from 1 to 10% by weight, based on the one-component plastic precursor, in particular the one-component isocyanate-containing composition.

Where the aldimine-containing compound of the formula (I) is a reaction product having free isocyanate groups and obtained from an isocyanate-containing polyurethane polymer and an aldimine of the formula (XI), the content of the aldimine-containing compound AC in the one-component plastic precursor may also be toward 100% by weight since such a composition crosslinks under the influence of water.

It is advantageous if the one-component isocyanate-containing composition contains at least one catalyst CAT-1 in addition to the aldimine-containing compound of the formula (I) and to the polyurethane polymer P.

Compounds which have a long shelf-life together with isocyanate groups and which accelerate the reactions of the isocyanate groups, in particular those with aldimino groups, which lead to the curing of the composition are suitable as catalyst CAT-1. For example organic carboxylic acids, such as benzoic acid, salicylic acid or 2-nitrobenzoic acid, organic carboxylic anhydrides, such as phthalic anhydride or hexahydrophthalic anhydride, silyl esters of organic carboxylic acids, organic sulfonic acids, such as methanesulfonic acid, p-toluenesulfonic acid or 4-dodecylbenzenesulfonic acid, or further organic or inorganic acids; metal compounds, for example tin compounds, for example dialkyltin dicarboxylates, such as dibutyltin diacetate, dibutyltin bis(2-ethylhexanoate), dibutyltin dilaurate, dibutyltin dipalmitate, dibutyltin distearate, dibutyltin dioleate, dibutyltin dilinoleate, dibutyltin dilinolenate, dibutyltin diacetylacetonate, dibutyltin maleate, dibutyltin bis(octylmaleate), dibutyltin phthalate, dimethyltin dilaurate, dioctyltin diacetate or dioctyltin dilaurate, dialkyltinmercaptides, such as dibutyltin bis(2-ethylhexylmercaptoacetate) or dioctyltin bis(2-ethylhexylmercaptoacetate), dibutyltin dichloride, monobutyltin trichloride, alkyltin thioesters, dibutyltin oxide, dioctyltin oxide, tin(II) carboxylates, such as tin(II) octanoate, tin(II) 2-ethylhexanoate, tin(II) laurate, tin(II) oleate or tin(II) naphthenate, stannoxanes, such as lauryl stannoxane, bismuth compounds, such as bismuth(III) octanoate, bismuth(III) neodecanoate or bismuth(III) oxinates; weakly basic tertiary amine compounds, such as, for example, 2,2'-dimorpholinodiethyl ether and other morpholine ether derivatives; and combinations of said compounds, in particular of acids and metal compounds or of metal compounds and compounds containing amino groups, should be mentioned as suitable catalysts CAT-1.

The one-component plastic precursor optionally contains further constituents, as are usually used according to the prior art. In particular, the one-component isocyanate-containing composition optionally contains one or more of the following auxiliaries and additives:

- plasticizers, for example esters of organic carboxylic acids or the anhydrides thereof, phthalates, such as, for example, dioctyl phthalate or diisodecyl phthalate, adipates, such as, for example, dioctyl adipate, sebacates, polyols, such as, for example, polyoxyalkylene polyols or polyester polyols, organic phosphoric acid and sulfonic acid esters or polybutenes;
- solvents, for example ketones, such as acetone, methyl ethyl ketone, diisobutyl ketone, acetonylacetone, mesityl oxide, and cyclic ketones, such as methylcyclohexanone and cyclohexanone; esters, such as ethyl acetate, propyl acetate or butyl acetate, formates, propionates or malonates; ethers, such as ketone ethers, ester ethers and dialkyl ethers, such as diisopropyl ether, diethyl ether, dibutyl ether, diethylene glycol diethyl ether and ethylene glycol diethyl ether; aliphatic and aromatic hydrocarbons, such as toluene, xylene, heptane, octane and different mineral oil fractions, such as naphtha, white spirit, petroleum ether or gasoline; halogenated hydrocarbons, such as methylene chloride; and N-alkylated lactams, such as, for example, N-methylpyrrolidone, N-cyclohexylpyrrolidone or N-dodecylpyrrolidone;
- inorganic and organic fillers, such as, for example, milled or precipitated calcium carbonates which are optionally coated with stearates, in particular finely divided coated calcium carbonate, carbon blacks, kaolins, aluminas, silicas, PVC powder or hollow spheres; fibers, for example of polyethylene; pigments;
- further catalysts customary in polyurethane chemistry;
- reactive diluents and crosslinking agents, for example polyisocyanates, such as MDI, PMDI, TDI, HDI, 1,12-dodecamethylene diisocyanate, cyclohexane 1,3- or 1,4-diisocyanate, IPDI, perhydro-2,4'- and -4,4'-diphenylmethane diisocyanate, 1,3- and 1,4-tetramethylxylylene diisocyanate, oligomers and polymers of these polyisocyanates, in particular isocyanurates, carbodiimides, uretonimines, biurets, allophanates and iminooxadiazinediones of said polyisocyanates, adducts of polyisocyanates with short-chain polyols, and adipic acid dihydrazide and other dihydrazides;
- latent polyamines, such as, for example, polyaldimines, polyketimines, polyenamines, polyoxazolidines, polyamines adsorbed on a zeolite or microencapsulated polyamines, and amine-metal complexes, preferably polyaldimines from the reaction of a primary aliphatic polyamine with an aldehyde, in particular an aldehyde A, such as, for example, 2,2-dimethyl-3-acyloxypropanal, in particular 2,2-dimethyl-3-lauroyloxypropanal, and complexes between methylenedianiline (MDA) and sodium chloride (obtainable as a dispersion in diethylhexyl phthalate or diisodecyl phthalate under the trade name Caytur® 21 from Crompton Chemical);
- drying agents, such as, for example, p-tosyl isocyanate and other reactive isocyanates, orthoformic acid esters, calcium oxide; vinyltrimethoxysilane or other rapidly hydrolyzing silanes, such as, for example, organoalkoxysilanes which have a functional group in the a position relative to the silane group, or molecular sieves;
- rheology modifiers, such as, for example, thickeners, for example urea compounds, polyamide waxes, bentonites or pyrogenic silicas;
- adhesion promoters, in particular silanes, such as, for example, epoxysilanes, vinylsilanes, (meth)acryloylsilanes, isocyanatosilanes, carbamatosilanes, S-(alkylcarbonyl)mercaptosilanes and aldiminosilanes, and oligomeric forms of these silanes;
- heat, light and UV stabilizers; flame-retardant substances;
- surface-active substances, such as, for example, wetting agents, leveling agents, deaerating agents or antifoams;
- biocides, such as, for example, algicides, fungicides or substances inhibiting fungal growth;

and further substances customarily used in one-component isocyanate-containing compositions.

The one-component plastic precursor, in particular the one-component isocyanate-containing composition, has a good shelf-life in the absence of the factors triggering crosslinking reactions of the reactive groups present in the plastic precursor, in particular of moisture, heat or UV radiation. In particular, the one-component isocyanate-containing composition has a good shelf-life in the absence of moisture, for example in a climatically tight packaging or arrangement, such as, for example, in a drum, a bag or a cartridge. In the present document, the terms "having a long shelf-life" and "shelf-life" in relation to a plastic precursor designate the fact that the viscosity of the plastic precursor during suitable storage in the time span considered does not increase or at most does not increase to such an extent that the plastic precursor remains usable in the intended manner.

Under the influence of moisture, for example on contact with humid air or after admixing of water, or on strong heating, or under the influence of UV radiation, or under the influence of a combination of these factors, the plastic precursor cures rapidly to give a high molecular weight plastic. In particular, the isocyanate-containing composition cures under the influence of moisture rapidly and completely to give a substantially nontacky polyurethane plastic. The curing takes place without bubble formation since some or all of the isocyanate groups react with the hydrolyzing aldimino groups, little or no $CO_2$ forming. The curing is additionally accelerated by the presence of catalysts for hydrolysis of the aldimino groups, for example the abovementioned organic carboxylic acids or sulfonic acids, without bubble formation occurring. The moisture required for the curing may originate from the air (atmospheric humidity), the plastic precursor curing from the outside to the inside by the diffusion of the moisture. The plastic precursor can, however, also be brought into contact with a water-containing component, for example by coating, for example with a smoothing composition, by spraying or by means of immersion methods, or a water-containing component may be added to the plastic precursor, for example in the form of a water-containing paste, which is homogeneously or heterogeneously mixed with the plastic precursor, for example via a static mixer.

As already mentioned, suitable plastic precursors which contain the aldimine-containing compounds of the formula (I) as constituents may also comprise two components. Suitable two-component plastic precursors consist of two components K1 and K2, at least one of the components K1 or K2 containing at least one aldimine-containing compound of the formula (I), and the mixture of the two components K1 and K2 leading to a high molecular weight plastic.

Two-component isocyanate-containing compositions in which the component K1 comprises at least one polyisocyanate and/or at least one isocyanate-containing polyurethane polymer P and the component K2 comprises at least one polyol and/or at least one polyamine, and at least one of the components K1 or K2 contains at least one aldimine-containing compound of the formula (I), are particularly suitable as two-component plastic precursors.

The polyisocyanates mentioned for the preparation of the isocyanate-containing polyurethane polymer P are suitable as polyisocyanate of component K1. PMDI ("polymeric MDI"), known, for example, under trade names such as Desmodur® VL, Desmodur® VL 50, Desmodur® VL R 10, Desmodur® VL R 20, Desmodur® VKS 20 F (all from Bayer), Isonate® M 309, Voranate® M 229, Voranate M® 580 (all from Dow) or Lupranat® M 10 R (from BASF), and forms of MDI which are liquid at room temperature (so-called "modified MDI"), which are mixtures of MDI with MDI derivatives, such as, for example, MDI-carbodiimides or MDI-uretonimines, known, for example, under trade names such as Desmodur® CD, Desmodur® PF, Desmodur® PC (all from Bayer), are particularly suitable.

Particularly suitable isocyanate-containing polyurethane polymers P of component K1 are those which were prepared using MDI, HDI, TDI or IPDI.

Suitable polyols of component K2 are the same polyols which have already been mentioned as suitable for the preparation of the isocyanate-containing polyurethane polymer P. Highly functional polyols, for example triols, tetrols and polyols having a higher functionality; amine-containing polyether polyols or polyether polyols initiated with amines (for example ethylenediamine); short-chain polyether polyols having molecular weights of from 300 to 2000; hydrophobic polyols, in particular fatty polyols, such as, for example, castor oil or the polyols known under the trade name Sovermol® from Cognis; and also diol chain extenders, such as 1,4-butanediol, 1,6-hexanediol, ethylene glycol; diethylene glycol, propylene glycol, dipropylene glycol, 1,4-bis(hydroxyethyl)hydroquinone, 1,4-cyclohexanediol or N,N'-bis(hydroxyethyl)piperazine, are particularly suitable.

Suitable polyamines of component K2 are firstly primary aliphatic polyamines, such as those described as amines C; and secondly polyaminoamides; secondary aliphatic polyamines, such as, for example, N,N'-dibutylethylenediamine; N,N'-di-tert-butylethylenediamine, N,N'-diethyl-1,6-hexanediamine, 1-(1-methylethylamino)-3-(1-methylethylaminomethyl)-3,5,5-trimethylcyclohexane (Jefflink® 754 from Huntsman), N4-cyclohexyl-2-methyl-N2-(2-methylpropyl)-2,4-pentanediamine, N,N'-dialkyl-1,3-xylylenediamine, bis(4-(N-alkylamino)cyclohexyl)methane, N-alkylated polyetheramines, products from the Michael-like addition reaction of the primary aliphatic polyamines mentioned by way of example with Michael acceptors, such as maleic acid diesters, fumaric acid diesters, citraconic acid diesters, acrylic acid esters, methyacrylic acid esters, cinnamic acid esters, itaconic acid diesters, vinylphosphonic acid diesters, aryl vinylsulfonates, vinyl sulfones, vinylnitriles, 1-nitroethylenes or Knoevenagel condensates, such as, for example, those from malonic acid diesters and aldehydes, such as formaldehyde, acetaldehyde or benzaldehyde; aliphatic polyamines having primary and secondary amino groups, such as, for example, N-butyl-1,6-hexanediamine; and primary and/or secondary aromatic polyamines, such as, for example, m- and p-phenylenediamine, 4,4'-diaminodiphenylmethane (MDA), 3,3'-dichloro-4,4'-diaminodiphenylmethane (MOCA), mixtures of 3,5-dimethylthio-2,4- and -2,6-toluoylenediamine (obtainable as Ethacure® 300 from Albemarle), mixtures of 3,5-diethyl-2,4- and -2,6-toluoylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzenesulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (obtainable as Versalink® from Air Products), 1,2-bis(2-aminophenylthio)ethane, N,N'-dialkyl-p-phenylenediamine, N,N'-dialkyl-4,4'-diaminodiphenylmethane, 2-methylpropyl 4-chloro-3,5-diaminobenzoate and tert-butyl 4-chloro-3,5-diaminobenzoate.

It is also possible to use polyamines in the form of derivatives in which all or some of the amino groups are blocked and react with isocyanates only after their activation by hydrolysis and/or heating. Examples of such polyamine derivatives having blocked amino groups are polyfunctional aldimines, ketimines, enamines, oxazolidines, aminals, ammonium carbonates, amine/carbonic acid salts (carbamates) or amine-metal complexes. Polyamines adsorbed on zeolite or microencapsulated polyamines may also be used.

The two-component isocyanate-containing composition contains at least one aldimine-containing compound of the formula (I) in one of the preferred embodiment already described above in detail.

Typically, the aldimine-containing compound of the formula (I) is present in an amount of from 0.1 to 50% by weight, preferably from 0.5 to 30% by weight and in particular from 1 to 20% by weight, based on the two-component isocyanate-containing composition.

It is advantageous if the two-component isocyanate-containing composition contains at least one catalyst CAT-2. Compounds which accelerate the curing of the composition are suitable as catalyst CAT-2. Firstly, the abovementioned catalysts CAT-1 and further catalysts, for example compounds of zinc, manganese, iron, chromium, cobalt, copper, nickel, molybdenum, lead, cadmium, mercury, antimony, vanadium, titanium, zirconium or potassium, such as zinc(II) acetate, zinc(II) 2-ethylhexanoate, zinc(II) laurate, zinc(II) oleate, zinc(II) naphthenate, zinc(II) acetylacetonate, zinc(II) salicylate, manganese(II) 2-ethylhexanoate, iron(III) 2-ethylhexanoate, iron(III) acetylacetonate, chromium(III) 2-ethylhexanoate, cobalt(II) naphthenate, cobalt(II) 2-ethylhexanoate, copper(II) 2-ethylhexanoate, nickel(II) naphthenate, phenylmercury neodecanoate, lead(II) acetate, lead(II) 2-ethylhexanoate, lead(II) neodecanoate, lead(II) acetylacetonate, aluminum lactate, aluminum oleate, aluminum(III) acetylacetonate, diisopropoxytitanium bis(ethylacetoacetate), dibutoxytitanium bis(ethylacetoacetate), dibutoxytitanium bis(acetylacetonate), potassium acetate, potassium octanoate; tertiary amine compounds, such as triethylamine, tributylamine, N-ethyldiisopropylamine, N,N,N',N'-tetramethylethylenediamine, pentamethyldiethylenetriamine and higher homologues thereof, N,N,N',N'-tetramethylpropylenediamine, pentamethyldipropylenetriamine and higher homologues thereof, N,N,N',N'-tetramethyl-1,3-butanediamine, N,N,N'N'-tetramethyl-1,6-hexanediamine, bis(dimethylamino)methane, N,N-dimethylbenzylamine, N,N-dimethylcyclohexylamine, N-methyldicyclohexylamine, N,N-dimethylhexadecylamine, bis(N,N-diethylaminoethyl) adipate, N,N-dimethyl-2-phenylethylamine, tris(3-dimethylaminopropyl)amine, 1,4-diazabicyclo[2.2.2]octane, 1,8-diazabicyclo[5.4.0]undec-7-ene (DBU), N-methylmorpholine, N-ethylmorpholine, N-cocomorpholine, N,N'-dimethylpiperazine, N-methyl-N'-dimethylaminoethylpiperazine, bis(dimethylaminoethyl)piperazine, 1,3,5-tris(dimethylaminopropyl)hexahydrotriazine or bis(2-dimethylaminoethyl) ether; aromatic nitrogen compounds, such as 4-dimethylaminopyridine, N-methylimidazole, N-vinylimidazole or 1,2-dimethylimidazole; amidines and guanidines, such as 1,1,3,3-tetramethylguanidine; tertiary amine compounds containing active hydrogen atoms, such as triethanolamine, triisopropanolamine, N-methyldiethanolamine, N,N-dimethylethanolamine, 3-(dimethylamino)propyldiisopropanolamine, bis(3-(dimethylamino)propyl)isopropanolamine, bis(3-dimethylaminopropyl)amine, 3-(dimethylamino)propylurea, Mannich bases, such as 2,4,6-tris(dimethylaminomethyl)phenol or 2,4,6-tris(3-(dimethylamino)propylaminomethyl)phenol, N-hydroxypropylimidazole, N-(3-aminopropyl)imidazole, and alkoxylation and polyalkoxylation products of these compounds, for example dimethylaminoethoxyethanol; organic ammonium compounds, such as benzyltrimethylammonium hydroxide, or alkoxylated tertiary amines; so-called "delayed action" catalysts, which are modifications of known metal or amine catalysts, such as reaction products of tertiary amines and carboxylic acids or phenols, for example of 1,4-diazabicyclo-[2.2.2]octane or DBU and formic acid or acetic acid; and combinations of said compounds, in particular of compounds containing metal and amino groups, should be mentioned as suitable catalysts CAT-2.

In addition to the aldimine-containing compound of the formula (I), to the polyisocyanate or isocyanate-containing polyurethane polymer P, to the polyol and/or polyamine and to the optionally present catalyst CAT-2, the two-component isocyanate-containing composition may contain further constituents, it being possible to use the same plasticizers, solvents, fillers, catalysts, reactive diluents and crosslinking agents, latent polyamines, drying agents, rheology modifiers, adhesion promoters, stabilizers, surface-active substances and biocides as already mentioned for the one-component composition, and further substances customarily used in two-component polyurethane compositions. The division of these additional constituents between the components K1 and K2 is effected in the manner known to the person skilled in the art for two-component polyurethane compositions.

When stored separately from one another, the components K1 and K2 each have a long shelf-life. In particular, the component K1 must be prepared and stored in the absence of moisture.

The two components K1 and K2 are mixed with one another only shortly before application in a suitable manner, it being necessary to ensure that as little air as possible enters the mixed composition during the mixing process and that a suitable mixing ratio is maintained. As soon as the two components come into contact with one another, the reactive constituents present in them begin to react with one another and thus lead to the curing of the mixed two-component composition. In particular, the isocyanate groups of the component K1 react with the partly or completely hydrolyzed aldimino groups of the component K1 or K2 and with the hydroxyl and/or amino groups of the component K2. The curing of the mixed two-component composition can be effected at room temperature; optionally, it can also be accelerated by supplying heat, in particular when the composition contains slowly reacting polyols or polyisocyanates, or when it contains thermally latent polyamines, such as amine-metal complexes or micro encapsulated polyamines, which react with the isocyanate groups only after an activation temperature, for example 80-200° C., has been exceeded.

The mixing ratio between the components K1 and K2 is usually chosen so that a certain excess of isocyanate groups relative to groups reacting with isocyanate groups, such as aldimino, hydroxyl and amino groups, is present. Usually, the mixing ratio is chosen so that the ratio ([OH]+[NH])/[NCO] has a value of from 0.5 to 0.95. This ensures that the mixed two-component composition cures to give a polymeric material, excess isocyanate groups reacting either with moisture from the component K2 or with moisture from the air. It must also be ensured that not too much time elapses between the mixing of the components K1 and K2 and the application to a surface of a substrate, since excessive preliminary reaction before the application makes it more difficult to form good adhesion to the substrate.

Because the aldimines of the formula (XI), the aldimine-containing compounds of the formula (I) themselves as well as the aldehydes A liberated on hydrolysis of these substances are free of odor, the plastic precursors described cure without formation of an odor. They can therefore also be used for applications requiring freedom from odor, such as, for example, for adhesive bonds, seals, coatings or coverings in the interior of vehicles or buildings. Such applications are, for example, adhesives, sealants, coatings or floor coverings in industrial manufacture or repair or in civil engineering or building construction or interior finishing of means of transport or structures. Applications as resilient adhesive in the manufacture of water or land vehicles, in particular automobiles, ships, buses, trucks or trains, and applications as resilient sealant in the manufacture of means of transport or structures should especially be mentioned.

EXAMPLES

Description of the Methods of Measurement

The infrared spectra were measured on an FT-IR apparatus 1600 from Perkin Elmer (horizontal ATR measuring unit with ZnSe crystal); the samples were applied undiluted as films. The absorption bands are stated in wave numbers ($cm^{-1}$) (measuring window: 4000-650 $cm^{-1}$).

$^1$H-NMR spectra were measured on a spectrometer of the type Bruker DPX-300 at 300.13 MHz; the chemical shifts δ are stated in ppm relative to tetramethylsilane (TMS), and coupling constants J are stated in Hz. The coupling patterns (t, m) were stated even if they are only pseudocoupling patterns.

The viscosity was measured on a thermostatted Physica UM cone-and-plate viscometer (cone diameter 20 mm, cone angle 1°, distance from cone apex to plate 0.05 mm, shear rate from 10 to 1000 $s^{-1}$).

The total content of aldimino groups and free amino groups in the compounds prepared ("amine content") was determined titrimetrically (with 0.1N $HClO_4$ in glacial acetic acid, against crystal violet) and is always stated in mmol $NH_2/g$ (even if they are only primary amino groups).

Aldimines of the Formula (XI) Containing a Free Hydrogen

Aldimine AL1

40.64 g (0.143 mol) of 2,2-dimethyl-3-lauroyloxypropanal were initially introduced under a nitrogen atmosphere in a round-bottomed flask. 11.68 g (0.133 mol) of N-methyl-1,3-propanediamine were added from a dropping funnel in the course of 5 minutes with vigorous stirring, the temperature of the reaction mixture increasing to 38° C. Thereafter, the volatile constituents were removed in vacuo (10 mbar, 80° C.). 49.8 g of a colorless, clear and odorless liquid which had a low viscosity at room temperature and an amine content of 5.20 mmol $NH_2/g$ were obtained. The product is present for the most part in the open-chain (aldimine) form.

IR: 3329 (N—H), 2954sh, 2922, 2852, 789, 1736 (C=O), 1668 (C=N), 1466, 1419sh, 1392, 1374, 1348, 1300, 1249, 1234, 1160, 1112, 1069, 1058, 1021, 996, 938, 886, 876, 820, 722.

$^1$H-NMR ($CDCl_3$, 300 K): δ 7.53 (s, 1H, CH=N), 4.01 (s, 2H, $CH_2O$), 3.44 (t, 2H, CH=$NCH_2CH_2$), 2.58 (t, 2H, $NHCH_2$), 2.42 (s, 3H, $CH_3NH$), 2.30 (t, 2H, $CH_2CO$), 1.76 (t,

2H, CH=NCH$_2$CH$_2$), 1.61 (m, 3H, CH$_2$CH$_2$CO and CH$_3$NHCH$_2$), 1.27 (m, 16H, CH$_3$—(CH$_2$)$_8$—CH$_2$CH$_2$CO), 1.10 (S, 6H, C(CH$_3$)$_2$—CH$_2$O), 0.89 (t, 3H, CH$_3$—(CH$_2$)$_{10}$—CO).

Aldimine AL2

30.13 g (0.106 mol) of 2,2-dimethyl-3-lauroyloxypropanal were initially introduced under a nitrogen atmosphere in a round-bottomed flask. 15.00 g (0.096 mol) of N-cyclohexyl-1,3-propanediamine were added from a dropping funnel in the course of 5 minutes with vigorous stirring, the temperature of the reaction mixture increasing to 36° C. Thereafter, the volatile constituents were removed in vacuo (10 mbar, 80° C.). 43.2 g of a colorless, clear and odorless liquid which had a low viscosity at room temperature and an amine content of 4.39 mmol NH$_2$/g were obtained. The product is present for the most part in the open-chain (aldimine) form.

IR: 3308 (N—H), 2921, 2851, 2659, 1737 (C=O), 1668 (C=N), 1465, 1449, 1418sh, 1393, 1366, 1346, 1301, 1248, 1158, 1111, 1068, 1020, 1002, 938, 888, 845, 797, 721.

$^1$H-NMR (CDCl$_3$, 300 K): δ 7.53 (s, 1H, CH=N), 4.01 (s, 2H, CH$_2$O), 3.43 (t, 2H, CH=NCH$_2$CH$_2$), 2.65 (t, 2H, NHCH$_2$), 2.40 (s, 1H, Cy—C$^1$HNH), 2.29 (t, 2H, CH$_2$CO), 1.86 (m, 2H, 2 Cy—H), 1.72 (m, 4H, 2 Cy—H and CH=NCH$_2$CH$_2$), 1.60 (m, 3H, CH$_2$CH$_2$CO and CH$_3$NHCH$_2$), 1.26 (m, 22H, CH$_3$—(CH$_2$)$_8$—CH$_2$CH$_2$CO and 6 Cy—H), 1.09 (s, 6H, C(CH$_3$)$_2$—CH$_2$O), 0.88 (t, 3H, CH$_3$—(CH$_2$)$_{10}$—CO).

Aldimine AL3

69.31 g (0.244 mol) of 2,2-dimethyl-3-lauroyloxypropanal were initially introduced under a nitrogen atmosphere in a round-bottomed flask. 14.72 g (0.112 mol) of dipropylenetriamine were added from a dropping funnel in the course of 5 minutes with vigorous stirring, the temperature of the reaction mixture increasing to 36° C. Thereafter, the volatile constituents were removed in vacuo (10 mbar, 80° C.). 79.7 g of a colorless, clear and odorless liquid which had a low viscosity at room temperature and an amine content of 4.17 mmol NH$_2$/g were obtained. The product is present for the most part in the open-chain (aldimine) form.

IR: 3308 (N—H), 2952sh, 2921, 2851, 1737 (C=O), 1667 (C=N), 1466, 1418sh, 1393, 1373, 1348, 1301, 1248, 1234, 1159, 1111, 1070, 1019, 1001, 936, 875, 722.

$^1$H-NMR (CDCl$_3$, 300 K): δ 7.53 (s, 2H, CH=N), 4.01 (s, 4H, CH$_2$O), 3.42 (t, 4H, CH=NCH$_2$CH$_2$), 2.61 (t, 4H, NHCH$_2$), 2.29 (t, 4H, CH$_2$CO), 1.73 (m, 4H, CH=NCH$_2$CH$_2$), 1.59 (m, 5H, CH$_2$CH$_2$CO and CH$_2$NHCH$_2$), 1.25 (m, 32H, CH$_3$—(CH$_2$)$_8$—CH$_2$CH$_2$CO), 1.09 (s, 12H, C(CH$_3$)$_2$—CH$_2$O), 0.87 (t, 6H, CH$_3$—(CH$_2$)$_{10}$—CO).

Aldimine AL4

34.15 g (0.120 mol) of 2,2-dimethyl-3-lauroyloxypropanal were initially introduced under a nitrogen atmosphere in a round-bottomed flask. 12.02 g (0.056 mol) of bishexamethylenetriamine (BHMT-HP; Invista) were added from a dropping funnel in the course of 5 minutes with vigorous stirring, the temperature of the reaction mixture increasing to 35° C. Thereafter, the volatile constituents were removed in vacuo (10 mbar, 80° C.). 43.6 g of a colorless, clear and odorless liquid which had a low viscosity at room temperature and an amine content of 3.68 mmol NH$_2$/g were obtained. The product is present for the most part in the open-chain (aldimine) form.

IR: 2922, 2851, 1737 (C=O), 1668 (C=N), 1465, 1417, 1393, 1373, 1340, 1248, 1234, 1159, 1111, 1020, 1003, 933, 870, 722.

$^1$H-NMR (CDCl$_3$, 300 K): δ 7.52 (s, 2H, CH=N), 4.02 (s, 4H, CH$_2$O), 3.36 (t, 4H, CH=NCH$_2$CH$_2$), 2.59 (t, 4H, NHCH$_2$), 2.29 (t, 4H, CH$_2$CO), 1.76-1.51 (m, 13H, CH=NCH$_2$CH$_2$), NHCH$_2$CH$_2$, CH$_2$CH$_2$CO and CH$_2$NHCH$_2$), 1.27 (m, 40H, CH$_3$—(CH$_2$)$_8$—CH$_2$CH$_2$CO and NHCH$_2$CH$_2$CH$_2$), 1.10 (s, 12H, C(CH$_3$)$_2$—CH$_2$O), 0.88 (t, 6H, CH$_3$—(CH$_2$)$_{10}$—CO).

Aldimine AL5

30.28 g (0.106 mol) of 2,2-dimethyl-3-lauroyloxypropanal were initially introduced under a nitrogen atmosphere in a round-bottomed flask. 5.00 g (0.049 mol) of diethylenetriamine were added from a dropping funnel in the course of 5 minutes with vigorous stirring. Thereafter, the volatile constituents were removed in vacuo (10 mbar, 80° C.). 33.1 g of a colorless, clear and odorless liquid which had a low viscosity at room temperature and an amine content of 4.07 mmol NH$_2$/g were obtained. The product is present for the most part in the open-chain (aldimine) form.

IR: 3348 (N—H), 2952, 2921, 2852, 1735 (C=O), 1668 (C=N), 1632, 1465, 1417, 1393, 1373, 1345, 1248, 1232, 1158, 1110, 1056, 1022, 1005, 986, 931, 903, 875, 820, 721.

Aldimine AL6

20.97 g (0.074 mol) of 2,2-dimethyl-3-lauroyloxypropanal were initially introduced under a nitrogen atmosphere in a round-bottomed flask. 10.00 g (0.067 mol) of triethylene glycol monoamine (Jeffamine® XTA-250; Huntsman) were added from a dropping funnel in the course of 5 minutes with vigorous stirring, the temperature of the reaction mixture increasing to 33° C. Thereafter, the volatile constituents were removed in vacuo (10 mbar, 80° C.). 29.5 g of a colorless, clear and odorless liquid which had a low viscosity at room temperature and an amine content of 2.21 mmol NH$_2$/g were obtained. The product is present for the most part in the open-chain (aldimine) form.

IR: 3444br (O—H), 2952sh, 2921, 2852, 1736 (C=O), 1668 (C=N), 1466, 1418, 1394, 1374, 1366, 1350, 1301sh, 1248, 1145sh, 1116, 1067, 1023sh, 998sh, 932, 890, 829, 722.

$^1$H-NMR (CDCl$_3$, 300 K): δ 7.59 (s, 1H, CH=N), 4.03 (s, 2H, CH$_2$O), 3.79-3.59 (m, 12H, HOCH$_2$CH$_2$OCH$_2$CH$_2$OCH$_2$CH$_2$N), 3.47 (s, 1H HOCH$_2$), 2.31 (t, 2H, CH$_2$CO), 1.61 (m, 2H, CH$_2$CH$_2$CO), 1.27 (m, 16H, CH$_3$—(CH$_2$)$_8$—CH$_2$CH$_2$CO), 1.11 (s, 6H, C(CH$_3$)$_2$—CH$_2$O), 0.87 (t, 3H, CH$_3$—(CH$_2$)$_{10}$—CO).

Aldimine AL7

34.48 g (0.121 mol) of 2,2-dimethyl-3-lauroyloxypropanol were initially introduced under a nitrogen atmosphere in a round-bottomed flask. 20.00 g (0.117 mol) of isophoronediamine (Vestamin® IPD, Degussa) were added from a dropping funnel in the course of 15 minutes with vigorous stirring. Thereafter, the volatile constituents were removed in vacuo (10 mbar, 80° C.). 25.25 g (0.121 mol) of isobornyl acrylate (SR-506, Sartomer) were added at room temperature to the clear, colorless oil thus obtained. Stirring was effected for 30 minutes at room temperature and the mixture was then warmed up to 85° C. and kept at this temperature for 24 hours. The volatile constituents were then removed in a high vacuum (100° C.). 72.0 g of a colorless, clear and odorless liquid which had a low viscosity at room temperature and an amine content of 3.09 mmol NH$_2$/g were obtained. The product is present for the most part in the open-chain (aldimine) form.

IR: 3322 (N—H), 2950, 2923, 2871, 2852, 1732 (C=O), 1668 (C=N), 1457, 1418sh, 1388sh, 1377, 1364, 1310, 1294, 1248, 1196, 1165, 1110, 1053, 1015, 987, 969, 942, 931sh, 914, 893, 863, 840, 796, 722.

Aldimine AL8 (Comparison)

48.18 g (0.243 mol) of 3-phenoxybenzaldehyde were initially introduced under a nitrogen atmosphere in a round-bottomed flask. 20.00 g (0.227 mol) of N-methyl-1,3-propanediamine were added in the course of 5 minutes from a dropping funnel with vigorous stirring, the temperature of the reaction mixture increasing to 40° C. The volatile constituents were then removed in vacuo (10 mbar, 80° C.). 63.7 g of a pale yellow, clear and strongly smelling liquid which had a low viscosity at room temperature and an amine content of 7.08 mmol $NH_2$/g were obtained. The majority of the product is present in the cyclic (tetrahydropyrimidine) form.

IR: 3270 (N—H), 3060, 3036, 2978, 2940, 2837, 2773, 2692, 1935, 1865, 1778, 1702, 1645, 1582, 1483, 1456, 1442, 1418, 1370, 1353, 1308, 1236, 1210, 1188, 1163, 1128, 1108, 1072, 1053, 1023, 990, 964, 937, 917, 900, 889, 877, 839, 775, 748, 690.

$^1$H-NMR ($CDCl_3$, 300 K): δ 7.42-7.28 (m, 5 Ar—H), 7.16-7.01 (m, 4 Ar—H), 3.74 (s, 1H, Ar—CH(NH)N), 3.14 (m, 2H, $HNCH^{eq}H^{ax}$ and $CH_3NCH^{eq}H^{ax}$), 2.78 (m, 1H, $HNCH^{eq}H^{ax}$), 2.35 (m, 1H, $CH_3NCH^{eq}H^{ax}$), 2.06 (s, 3H, $CH_3N$), 1.90 (m, 1H, $CH_3NCH_2CH^{eq}H^{ax}$) 1.58 (m, 2H, $CH_3NCH_2CH^{eq}H^{ax}$ and $HNCH_2$).

Aldimine AL9

28.06 g (0.099 mol) of 2,2-dimethyl-3-lauroyloxypropanal were initially introduced under a nitrogen atmosphere in a round-bottomed flask. 10.00 g (0.095 mol) of 2-(2-aminoethoxy)ethanol (Diglycolamine® Agent; Huntsman) were added in the course of 3 minutes from a dropping funnel with vigorous stirring, the temperature of the reaction mixture increasing to 40° C. The volatile constituents were then removed in vacuo (10 mbar, 80° C.). 36.3 g of a colorless, clear and odorless liquid which had a low viscosity at room temperature and an amine content of 2.58 mmol $NH_2$/g were obtained. The product is present for the most part in the open-chain (aldimine) form.

IR: 3435br (O—H), 2954sh, 2922, 2852, 1736 (C=O), 1668 (C=N), 1466, 1418, 1394, 1375, 1248, 1233, 1160, 1127, 1062, 1022, 933, 893, 813, 721.

$^1$H-NMR ($CDCl_3$, 300 K): δ 7.59 (s, 1H, CH=N), 4.03 (s, 2H, $CH_2O$), 3.71 (m, 4H, $HOCH_2CH_2OCH_2CH_2N$), 3.58 (m, 4H, $HOCH_2CH_2OCH_2CH_2N$), 2.44 (br s, 1H $HOCH_2$), 2.30 (t, 2H, $CH_2CO$), 1.61 (m, 2H, $CH_2CH_2CO$), 1.26 (m, 16H, $CH_3$—$(CH_2)_8$—$CH_2CH_2CO$), 1.11 (s, 6H, $C(CH_3)_2$—$CH_2O$), 0.88 (t, 3H, $CH_3$—$(CH_2)_{10}$—CO)

Aldimine AL10

34.51 g (0.121 mol) of 2,2-dimethyl-3-lauroyloxypropanal were initially introduced under a nitrogen atmosphere in a round-bottomed flask. 33.39 g of N-oleyl-1,3-propanediamine (Duomeen® O, Akzo Nobel; amine number=337 mg KOH/g) were added in the course of 5 minutes from a dropping funnel with vigorous stirring, the temperature of the reaction mixture increasing to 48° C. The volatile constituents were then removed in vacuo (10 mbar, 80° C.). 65.7 g of a colorless, clear and odorless liquid which had a low viscosity at room temperature and an amine content of 3.07 mmol $NH_2$/g were obtained. The product is present for the most part in the open-chain (aldimine) form.

IR: 3307 (N—H), 3001sh, 2954sh, 2921, 2851, 1739 (C=O), 1668 (C=N), 1464, 1393, 1375, 1347, 1301, 1248, 1158, 1114, 1067, 1020, 1000, 968, 935, 889, 721.

$^1$H-NMR ($CDCl_3$, 300 K): δ 7.53 (t, J=1.2) and 7.51 (s) (total 1H (ratio about 0.85/0.15), CH=N), 5.34 (m, 2H, $CH_2CH$=$CHCH_2$), 4.01 (s, 2H, $CH_2O$), 3.43 (t, 2H, CH=$NCH_2CH_2$), 2.60 (m, 4H, CH=$NCH_2CH_2CH_2$ and $NHCH_2$), 2.30 (t, 2H $CH_2CO$), 2.01 (m, 4H, $CH_2CH$=$CHCH_2$), 1.75 (m, 2H, CH=$NCH_2CH_2$), 1.60 (m, 3H, $CH_2CH_2CO$ and $CH_2NHCH_2$), 1.47 (m, 2H, $CH_2NHCH_2CH_2$), 1.26 (m, 38H, other $CH_2$ groups), 1.09 (s, 6H, $C(CH_3)_2$—$CH_2O$), 0.88 (t, 6H, both $CH_3CH_2CH_2$).

Aldimine AL11

40.00 g (0.141 mol) of 2,2-dimethyl-3-lauroyloxypropanal were initially introduced under a nitrogen atmosphere in a round-bottomed flask. 24.00 g (0.128 mol) of N-(2-ethylhexyl)-1,3-propanediamine (BASF) were added in the course of 5 minutes from a dropping funnel with vigorous stirring, the mixture was warmed up to 80° C. and at the same time the volatile constituents were removed in vacuo (10 mbar). 61.5 g of a colorless, clear and odorless liquid which had a low viscosity at room temperature and an amine content of 4.12 mmol $NH_2$/g were obtained. The product is present for the most part in the open-chain (aldimine) form.

IR: 3322 (N—H), 2955, 2922, 2870sh, 2852, 2824sh, 1738 (C=O), 1668 (C=N), 1464, 1393, 1376, 1342, 1300, 1248, 1235, 1157, 1114, 1069, 1020, 1000, 935, 894, 873, 766, 723.

Aldimine AL12

35.00 g (0.123 mol) of 2,2-dimethyl-3-lauroyloxypropanal were initially introduced under a nitrogen atmosphere in a round-bottomed flask. 36.31 g of N-tallowalkyl-1,3-propanediamine (Duomeen® T, Akzo Nobel; amine number=346 mg KOH/g) at 50° C. were added in the course of 5 minutes with vigorous stirring, the mixture was warmed up to 80° C. and at the same time the volatile constituents were removed in vacuo (10 mbar). 69.2 g of a dirty white, odorless body solid at room temperature and having an amine content of 3.20 mmol $NH_2$/g were obtained. The product is present for the most part in the open-chain (aldimine) form.

IR: 3316 (N—H), 2954sh, 2919, 2851, 2815sh, 1739 (C=O), 1668 (C=N), 1464, 1393, 1375, 1347, 1300, 1248, 1233, 1158, 1128sh, 1114, 1068, 1021, 1000, 968, 936, 917sh, 889, 873, 721.

Aldimine-Containing Compounds Formula (I)

Example 1

Aldimine-Containing Compound AC1

1.74 g (13.9 mmol of NCO) of 4,4'-diphenylmethane diisocyanate (MDI; Desmodur® 44 MC L, Bayer) were initially introduced under a nitrogen atmosphere in a round-bottomed flask and heated to 50° C. 10.00 g (13.9 mmol) of aldimine AL3 were added in the course of 5 minutes from a dropping funnel with thorough stirring and the mixture was stirred at 50° C. for one hour. A colorless, clear and odorless liquid which had a high viscosity at room temperature and an amine content of 2.37 mmol $NH_2$/g and reacted neutrally to a moistened pH paper was obtained.

IR: 3300 (N—H), 2952sh, 2922, 2851, 1735 (C=O), 1664 (C=N), 1647sh, 1595, 1527sh, 1513, 1466, 1416, 1395, 1375, 1305, 1244, 1215, 1196, 1162, 1112, 1056, 1018, 1000, 939, 918sh, 851, 813, 777, 751, 721.

Example 2

Aldimine-Containing Compound AC2

3.47 g (27.7 mmol of NCO) of 4,4'-diphenylmethane diisocyanate (MDI; Desmodur® 44 MC L, Bayer) were initially introduced under a nitrogen atmosphere in a round-bottomed flask and heated to 50° C. 10.00 g (13.9 mmol) of aldimine AL3 were added in the course of 5 minutes from a dropping funnel with thorough stirring and the mixture was stirred at 50° C. for one hour. A pale yellow, clear and odorless liquid which had a high viscosity at room temperature and reacted neutrally to a moistened pH paper was obtained.

IR: 3308 (N—H), 2954sh, 2922, 2852, 2266, (N=C=O), 1735 (C=O), 1665 (C=N), 1596, 1526sh, 1514, 1467, 1415, 1395, 1374, 1306, 1244, 1216, 1197, 1162, 1110, 1059, 1018, 1000, 940, 918sh, 854, 813, 781, 751, 721.

Example 3

Aldimine-Containing Compound AC3

12.94 g (103.4 mmol of NCO) of 4,4'-diphenylmethane diisocyanate (MDI; Desmodur® 44 MC L, Bayer) were initially introduced under a nitrogen atmosphere in a round-bottomed flask and heated to 50° C. 42.16 g (51.7 mmol) of aldimine AL4 were added in the course of 10 minutes from a dropping funnel with thorough stirring and the mixture was stirred at 50° C. for one hour. A light yellow, clear and odorless liquid which had a high viscosity at room temperature and reacted neutrally to a moistened pH paper was obtained.

IR: 3336 (N—H), 2922, 2852, 2265, (N=C=O), 1736 (C=O), 1666 (C=N), 1640, 1594, 1513, 1488, 1465, 1416, 1394, 1373, 1307, 1237, 1169, 1110, 1065, 1018, 1000 sh, 932, 918sh, 848, 812, 776, 754, 723.

Example 4

Aldimine-Containing Compound AC4

10.00 g (51.4 mmol of NCO) of 1,6-hexamethylene diisocyanate trimer (Desmodur® N-3300, Bayer; NCO content=21.61% by weight) were dissolved in 29.79 g of dry diisodecyl phthalate (DIDP; Palatinol® Z, BASF) under a nitrogen atmosphere in a round-bottomed flask. 19.79 g (102.9 mmol) of aldimine AL1 were added in the course of 10 minutes from a dropping funnel at room temperature with thorough stirring and the mixture was stirred for one hour. A colorless, clear and odorless liquid which had a low viscosity at room temperature and an amine content of 0.87 mmol $NH_2$/g and reacted neutrally to a moistened pH paper was obtained.

IR: 3423 (N—H), 3326 (N—H), 2954, 2924, 2853, 1726 (C=O), 1688, 1650, 1600, 1579, 1529, 1462, 1377, 1335, 1272, 1164, 1121, 1072, 1039, 985, 965, 948, 764, 742, 704.

Example 5

Aldimine-Containing Compound AC5

10.00 g (51.4 mmol of NCO) of 1,6-hexamethylene diisocyanate trimer (Desmodur® N-3300, Bayer; NCO content=21.61% by weight) were dissolved in 47.05 g of dry ethyl acetate under a nitrogen atmosphere in a round-bottomed flask. 37.05 g (102.9 mmol) of aldimine AL3 were added in the course of 10 minutes from a dropping funnel at room temperature with thorough stirring and the mixture was stirred for one hour. A colorless, clear and odorless liquid which had a low viscosity at room temperature and an amine content of 1.11 mmol $NH_2$/g and reacted neutrally to a moistened pH paper was obtained.

IR: 3422 (N—H), 3308 (N—H), 2954, 2924, 2853, 1727 (C=O), 1689, 1651, 1600, 1579, 1528, 1462, 1377, 1334, 1272, 1161, 1121, 1072, 1039, 995, 948, 870, 764, 742, 704.

Example 6

Aldimine-Containing Compound AC6

79.21 g (40.2 mmol of OH) of polyoxypropylenediol (Acclaim® 4200 N, Bayer; OH number 28.5 mg KOH/g), 10.79 g (43.1 mmol) of 4,4'-methylenediphenyl diisocyanate (MDI; Desmodur® 44 MC L, Bayer) and 10.00 g of diisodecyl phthalate (DIDP; Palatinol® Z, BASF) were reacted at 80° C. to give an NCO-terminated polyurethane polymer having a content of free isocyanate groups of 1.86% by weight and a viscosity at 20° C. of 24 Pa·s. 8.51 g (22.1 mmol) of aldimine AL1 were added to this polymer at room temperature and the mixture was thoroughly mixed by means of a centrifugal mixer (SpeedMixerm DAC 150, FlackTek Inc.). A clear, homogeneous and odorless liquid having a viscosity at 20° C. of 40 Pa·s was obtained.

Example 7

Aldimine-Containing Compound AC7

79.21 g (40.2 mmol of OH) of polyoxypropylenediol (Acclaim® 4200 N, Bayer; OH number 28.5 mg KOH/g), 10.79 g (43.1 mmol) of 4,4'-methylenediphenyl diisocyanate (MDI; Desmodur® 44 MC L, Bayer) and 10.00 g of diisodecyl phthalate (DIDP; Palatinol® Z, BASF) were reacted at 80° C. to give an NCO-terminated polyurethane polymer having a content of free isocyanate groups of 1.86% by weight and a viscosity at 20° C. of 24 Pa·s. 10.62 g (14.8 mmol) of aldimine AL3 were added to this polymer at room temperature and the mixture was thoroughly mixed by means of a centrifugal mixer (SpeedMixer™ DAC 150, FlackTek Inc.). A clear, homogeneous and odorless liquid having a viscosity at 20° C. of 29 Pa·s was obtained.

Example 8

Aldimine-Containing Compound AC8

79.21 g (40.2 mmol of OH) of polyoxypropylenediol (Acclaim® 4200 N, Bayer; OH number 28.5 mg KOH/g), 10.79 g (43.1 mmol) of 4,4'-methylenediphenyl diisocyanate (MDI; Desmodur® 44 MC L, Bayer) and 10.00 g of diisodecyl phthalate (DIDP; Palatinol® Z, BASF) were reacted at 80° C. to give an NCO-terminated polyurethane polymer having a content of free isocyanate groups of 1.86% by weight and a viscosity at 20° C. of 24 Pa·s. 17.03 g (44.3 mmol) of aldimine AL1 were added to this polymer at room temperature and the mixture was thoroughly mixed by means of a centrifugal mixer (SpeedMixer™ DAC 150, FlackTek Inc.). After 10 minutes, the NCO band in the FT-IR spectrum (at 2265 $cm^{-1}$) was no longer detectable. A clear, homogeneous and odorless liquid having a viscosity at 20° C. of 52 Pa·s and an amine content of 0.38 mmol $NH_2$/g was obtained.

Example 9

Aldimine-Containing Compound AC9

79.21 g (40.2 mmol of OH) of polyoxypropylenediol (Acclaim® 4200 N, Bayer; OH number 28.5 mg KOH/g), 10.79 g (43.1 mmol) of 4,4'-methylenediphenyl diisocyanate (MDI;

Desmodur® 44 MC L, Bayer) and 10.00 g of diisodecyl phthalate (DIDP; Palatinol® Z, BASF) were reacted at 80° C. to give an NCO-terminated polyurethane polymer having a content of free isocyanate groups of 1.86% by weight and a viscosity at 20° C. of 24 Pa·s. 31.85 g (44.3 mmol) of aldimine AL3 were added to this polymer at room temperature and the mixture was thoroughly mixed by means of a centrifugal mixer (SpeedMixer™ DAC 150, FlackTek Inc.). After 10 minutes, the NCO band in the FT-IR spectrum (at 2265 $cm^{-1}$) was no longer detectable. A clear, homogeneous and odorless liquid having a viscosity at 20° C. of 44 Pa·s and an amine content of 0.67 mmol $NH_2$/g was obtained.

Example 10

Aldimine-Containing Compound AC10

25.97 g (13.2 mmol of OH) of polyoxypropylenediol (Acclaim® 4200 N, Bayer; OH number 28.5 mg KOH/g), 51.95 g (32.4 mmol of OH) of polyol Caradol® MD34-02 (polypropylene oxide polyethylene oxide triol, OH number 35.0 mg KOH/g; Shell), 12.08 g (48.3 mmol) of 4,4'-methylenediphenyl diisocyanate (MDI; Desmodur® 44 MC L, Bayer) and 10.00 g of diisodecyl phthalate (DIDP; Palatinol® Z, BASF) were reacted at 80° C. to give an NCO-terminated polyurethane polymer having a content of free isocyanate groups of 2.07% by weight and a viscosity at 20° C. of 48 Pa·s. 18.95 g (49.3 mmol) of aldimine AL1 were added to this polymer at room temperature and the mixture was thoroughly mixed by means of a centrifugal mixer (SpeedMixer™ DAC 150, FlackTek Inc.). After 10 minutes, the NCO band in the FT-IR spectrum (at 2265 $cm^{-1}$) was no longer detectable. A clear, homogeneous and odorless liquid having a viscosity at 20° C. of 89 Pa·s and an amine content of 0.41 mmol $NH_2$/g was obtained.

Example 11

Aldimine-Containing Compound AC11

5.85 g (0.052 mol of NCO) of isophorone diisocyanate (Vestanat® IPDI, Degussa) were initially introduced under a nitrogen atmosphere in a round-bottomed flask. 10.00 g (0.026 mol) of aldimine AL1 were added in the course of 5 minutes from a dropping funnel at room temperature with stirring and the mixture was stirred for 30 minutes. 3.38 g (0.026 mol) of 2-hydroxyethyl methacrylate (HEMA; Bisomer® HEMA, Laporte) were added at room temperature to the clear, colorless oil thus obtained. Stirring was effected for 10 minutes, after which 2 mg of dibutyltin dilaurate were added, the mixture was heated to 75° C. and was kept at this temperature until the isocyanate band in the FT-IR spectrum (at 2253 $cm^{-1}$) had vanished (1 hour). A colorless, clear and odorless liquid which had a high viscosity and an amine content of 1.32 mmol $NH_2$/g was obtained.

IR: 3334 (N—H), 2952, 2923, 2852, 1719 (C=O), 1663sh (C=N), 1636 (C=C, C=O), 1527, 1459, 1377, 1364, 1341, 1296, 1234, 1164, 1060, 1044, 1017, 939, 891, 869, 814, 770, 721.

Example 12

Aldimine-Containing Compound AC12

5.48 g (26.0 mmol of NCO) of m-isopropenyl-α,α-dimethylbenzyl isocyanate (m-TMI; Cytec) were initially introduced under a nitrogen atmosphere in a round-bottomed flask. 10.00 g (26.0 mmol) of aldimine AL1 were added within 5 minutes from a dropping funnel at room temperature with stirring and the mixture was stirred until the isocyanate band in the FT-IR spectrum (at 2255 $cm^{-1}$) had vanished (30 minutes). A colorless, clear and odorless liquid which had a high viscosity and an amine content of 1.66 mmol $NH_2$/g was obtained.

IR: 3361 (N—H), 2953sh, 2922, 2852, 1736 (C=O), 1689, 1658, 1646, 1600, 1578, 1523, 1483, 1465, 1457, 1440sh, 1417sh, 1375, 1361sh, 1346sh, 1302, 1241, 1218sh, 1162, 1111, 1051, 1015, 1003, 938, 886, 797, 764, 722, 695.

Example 13

Aldimine-Containing Compound AC13

A mixture of 2.57 g (8.7 mmol) of trimethylolpropane triacrylate (TMPTA; SR-351, Sartomer) and 10.00 g (26.0 mmol) of aldimine AL1 were heated to 90° C. under a nitrogen atmosphere in a round-bottomed flask and kept at this temperature until the acryloyl band in the FT-IR spectrum ($\delta_{C=C\text{-}Hoop}$ at 808 $cm^{-1}$) had vanished (3 hours). A colorless, low-viscosity, clear and odorless liquid which had an amine content of 4.06 mmol $NH_2$/g was obtained.

IR: 2952sh, 2922, 2851, 2795sh, 2771sh, 1736 (C=O), 1667 (C=N), 1464, 1419, 1392sh, 1375, 1345, 1300, 1248, 1163, 1120, 1054, 1032, 1009, 934, 876, 783, 722.

Example 14

Aldimine-Containing Compound AC14

A mixture of 1.37 g (4.6 mmol) of trimethylolpropane triacrylate (TMPTA; SR-351, Sartomer) and 10.00 g (13.9 mmol) of aldimine AL3 were heated to 105° C. under a nitrogen atmosphere in a round-bottomed flask and kept at this temperature until the acryloyl band in the FT-IR spectrum ($\delta_{C=C\text{-}Hoop}$ at 808 $cm^{-1}$) had vanished (18 hours). A yellow, clear and odorless liquid which had high viscosity and an amine content of 3.48 mmol $NH_2$/g was obtained.

IR: 2952sh, 2922, 2851, 1736 (C=O), 1667 (C=N), 1465, 1418, 1392, 1374, 1347, 1300sh, 1246, 1163, 1113, 1054, 1057, 1017, 999, 935, 879, 781, 722.

Example 15

Aldimine-Containing Compound AC15

A mixture of 9.56 g (52.0 mmol of epoxy) of bisphenol A diglycidyl ether (DGEBA or BPADGE; Araldite® GY-250, Huntsman) and 20.00 g (52.0 mmol) of aldimine AL1 were heated to 70° C. under a nitrogen atmosphere in a round-bottomed flask and kept at this temperature until the epoxy bands in the FT-IR spectrum ($v_{C\text{-}Oasy}$ at 914 and 861 $cm^{-1}$) had vanished (16 hours). A colorless, high-viscosity, clear and odorless liquid which had an amine content of 3.50 mmol $NH_2$/g was obtained.

IR: 3420 (O—H), 3034, 2922, 2851, 2064, 1884, 1736 (C=O), 1667 (C=N), 1607, 1580, 1509, 1463, 1417, 1375, 1297, 1248, 1180, 1157, 1108, 1084, 1038, 933, 883, 827, 806, 767, 722.

One-Component Plastic Precursor

Examples 16 to 22 and Example 23

Comparison

For each example, 100.0 g of polyurethane polymer PP1, whose preparation is described below, were weighed into a polypropylene beaker having a screw closure and were placed under dry nitrogen. 0.3 g of a salicylic acid solution (5% by weight in diocytl adipate) was added to this and the aldimine of the formula (XI) stated in table 1 was added in the stated amount, the mixture was thoroughly mixed by means of a centrifugal mixer (SpeedMixer™ DAC 150, FlackTek Inc.), filled immediately thereafter into an aluminum tube coated on the inside and said aluminum tube was sealed air-tight. The amount of added aldimine of the formula (XI) corresponds for all examples to a ratio of 1.0/0.7 between the isocyanate groups in the polyurethane polymer and the sum of the reactive groups (aldimino groups plus amino or hydroxyl groups) in the aldimine.

The polyurethane polymer PP1 was prepared as follows:

1300 g of polyoxypropylenediol (Acclaim® 4200 N, Bayer; OH number 28.5 mg KOH/g), 2600 g of polyoxypropylenepolyoxyethylenetriol (Caradol® MD34-02, Shell; OH number 35.0 mg KOH/g), 605 g of 4,4'-methylenediphenyl diisocyanate (MDI; Desmodur® 44 MC L, Bayer) and 500 g of diisodecyl phthalate (DIDP; Palatinol® Z, BASF) were reacted at 80° C. to give an NCO-terminated polyurethane polymer having a titrimetrically determined content of free isocyanate groups of 2.07% by weight and a viscosity at 20° C. of 48 Pa·s.

The one-component plastic precursor thus obtained was tested for shelf-life, skin formation time, bubble formation, odor and mechanical properties after curing.

The shelf-life was determined via the change in the viscosity during storage at elevated temperatures. For this purpose, the plastic precursor was stored in a closed tube in an oven at 60° C. and its viscosity was measured a first time after a duration of storage of 12 hours and a second time after a duration of storage of 7 days. The shelf-life is obtained from the percentage increase in the second viscosity value compared with the first.

The results of the tests are shown in table 1.

TABLE 1

Composition and shelf-life of one-component plastic precursors.

| Example | Aldimine of the formula (I) | Aldimine addition [g] | [NCO] / [[OH]+[NH]] | Viscosity increase [%][a] |
|---|---|---|---|---|
| (Ref)[b] | — | — | — | 16 |
| 16 | AL1 | 6.6 | 1.0/0.7 | 18 |
| 17 | AL2 | 7.9 | 1.0/0.7 | 26 |
| 18 | AL3 | 8.3 | 1.0/0.7 | 18 |
| 19 | AL4 | 9.4 | 1.0/0.7 | 25 |
| 20 | AL5 | 8.5 | 1.0/0.7 | 27 |
| 21 | AL6 | 7.8 | 1.0/0.7 | 13 |
| 22 | AL7 | 11.2 | 1.0/0.7 | 23 |
| 23 (comparison) | AL8 | 4.9 | 1.0/0.7 | 42 |

[a] = (viscosity after 7 d/viscosity after 12 h − 1) × 100%.
[b] reference example without aldimine.

Table 1 shows that the one-component plastic precursors of examples 16 to 22, which contain aldimine-containing compounds of the formula (I) according to the invention, which were prepared in situ from the polyurethane polymer PP1 and the aldimines AL1 to AL7 of the formula (XI), have a comparably great viscosity increase after storage compared with the plastic precursor of the reference example, which contains no aldimine-containing compound. In comparison, the viscosity of the plastic precursor of comparative example 23, which contains an aldimine-containing compound according to the prior art, which was prepared in situ, from the polyurethane polymer PP1 and the aldimine AL8, increases substantially more sharply.

For determining the skin formation time (tack-free time), a small part of the plastic precursor stored for 12 hours at 60° C. and now at room temperature was applied in a layer thickness of 3 mm to cardboard and the time taken on gentle tapping of the plastic surface by means of an LDPE pipette for no residues to remain behind on the pipette for the first time was determined at 23° C. and 50% relative humidity.

For determining the mechanical properties after curing, a further part of the plastic precursor stored for 12 hours at 60° C. was cast as a film about 2 mm thick in a metal sheet coated with PTFE, whereupon the film was allowed to cure to a resilient plastic for 7 days at 23° C. and 50% relative humidity. The plastic film thus produced was tested according to DIN EN 53504 with regard to tensile strength, elongation at break and modulus of elasticity (pull-off rate: 200 mm/min). The bubble formation (on the basis of the amount of bubbles which occurred during the curing of the film) and the odor (by smelling with the nose at a distance of 10 cm, first on the freshly cast film and again on the completely cured film) were also qualitatively assessed.

The results of the tests are shown in table 2.

Table 2 shows that the one-component plastic precursors of examples 16 to 22, which in each case contain an aldimine-containing compound of the formula (I) according to the invention, prepared in situ, cure rapidly and without bubble formation, are odorless and, in the cured state, have good mechanical properties. In contrast, the plastic precursor of comparative example 23, which contains an aldimine-containing compound according to the prior art, prepared in situ, cures more slowly and with partial bubble formation and has a strong odor.

TABLE 2

Properties during and after the curing of one-component plastic precursors.

| | Example | | | | | | | 23 (comp.) |
|---|---|---|---|---|---|---|---|---|
| | 16 | 17 | 18 | 19 | 20 | 21 | 22 | |
| Skin formation (min.) | 35 | 45 | 35 | 50 | 40 | 35 | 45 | 90 |
| Bubble formation | none | none | none | none | none | none | none | few |
| Tensile strength (MPa) | 0.8 | 1.0 | 0.8 | 0.7 | 0.7 | 0.7 | 1.0 | 1.0 |
| Elongation at break (%) | 180 | 200 | 60 | 70 | 80 | 130 | 220 | 240 |
| Modulus of elasticity (MPa)[a] | 1.3 | 1.4 | 2.3 | 1.7 | 1.6 | 1.3 | 1.3 | 1.1 |
| Odor | none | none | none | none | none | none | none | strong |

[a] at 0.5-5.0% elongation.

Examples 24 and 25

In each case 50 g of one of the aldimine-containing compounds of the formula (I) which are shown in table 3 were weighed into a polypropylene beaker having a screw closure and were placed under dry nitrogen. 0.3 g of a salicylic acid solution (5% by weight in dioctyl adipate) was added thereto, the mixture was thoroughly mixed by means of a centrifugal mixer (SpeedMixer™ DAC 150, Flack Tek Inc.) and immediately thereafter filled into an internally coated aluminum tube and the latter was closed air-tight.

The one-component plastic precursor thus obtained was tested with regard to tack and, by the methods described for example 16, with regard to shelf-life, skin formation time, bubble formation, odor and mechanical properties after curing.

The test for tack was effected qualitatively by touching with the finger the surface of the plastic film prepared for determining the mechanical properties and partly cured for 1 day at 23° C. and 50% relative humidity.

The results of the tests are shown in table 3.

TABLE 3

Shelf-life, properties during and after curing
Properties during and after curing of one-component plastic precursors

| | Example | |
|---|---|---|
| | 24 | 25 |
| Aldimine-containing compound | AC6 | AC7 |
| Viscosity increase in % | 5 | 2 |
| Skin formation time (min) | 26 | 40 |
| Bubble formation | none | none |
| Tack | slight | none |
| Tensile strength (MPa) | 1.0 | 1.0 |
| Elongation at break (%) | 2900 | 100 |
| Modulus of elasticity (MPa)$^a$ | 0.9 | 1.8 |
| Odor | none | none |

$^a$at 0.5-5.0% elongation.

Table 3 shows that the one-component plastic precursors of examples 24 and 25, which in each case contain an aldimine-containing compound of the formula (I) AC6 and AC7, show only a slight viscosity increase during storage. During their use, they cure rapidly and without bubble formation, are odorless and, in the cured state, have good mechanical properties.

Examples 26 and 27

In each case one of the aldimine-containing compounds of the formula (I) which are shown in table 4 was weighed, together with the polyurethane polymer PP2, whose preparation is described below, in the stated amounts into a polypropylene beaker having a screw closure and was placed under dry nitrogen. 0.3 g of a salicylic acid solution (5% by weight in dioctyl adipate) was added thereto, the mixture was thoroughly mixed by means of a centrifugal mixer (SpeedMixer™ DAC 150, Flack Tek Inc.) and immediately thereafter filled into an internally coated aluminum tube and the latter was closed air-tight. The amount of added compound of the formula (I) corresponds to a ratio of 1/1 between the isocyanate groups in the polyurethane polymer and the aldimino groups in the compound of the formula (I).

The polyurethane polymer PP2 was prepared as follows:
3960 g of polyoxypropylenediol (Acclaim® 4200 N, Bayer; OH number 28.5 mg KOH/g), 540 g of 4,4'-methylenediphenyl diisocyanate (MDI; Desmodur® 44 MC L, Bayer) and 500 g of diisodecyl phthalate (DIDP: Palatinol® Z, BASF) were reacted at 80° C. to give an NCO-terminated polyurethane polymer having a titrimetrically determined content of free isocyanate groups of 1.86% by weight and a viscosity at 20° C. of 24 Pa·s.

TABLE 4

Composition of the one-component plastic precursors of examples 26 and 27.

| Example | Polyurethane polymer PP2 | Aldimine-containing compound |
|---|---|---|
| 26 | 23.04 g | AC8, 26.96 g |
| 27 | 30.13 g | AC9, 19.87 g |

The one-component plastic precursors thus obtained were tested by the methods described for example 16 with regard to shelf-life, skin formation time, bubble formation, odor and mechanical properties after curing and, by the method described for example 24, for tack. The results of the tests are shown in table 5.

TABLE 5

Shelf-life, properties during and after curing
Properties during and after curing of one-component plastic precursors

| | Example | |
|---|---|---|
| | 26 | 27 |
| Viscosity increase in % | 6 | 13 |
| Skin formation time (min) | 16 | 18 |
| Bubble formation | none | none |
| Tack | none | none |
| Tensile strength (MPa) | 3.5 | 1.0 |
| Elongation at break (%) | 2100 | 90 |
| Modulus of elasticity (MPa)$^a$ | 1.1 | 1.9 |
| Odor | none | none |

$^a$at 0.5-5.0% elongation.

Table 5 shows that the one-component plastic precursors of examples 26 and 27, which in each case contain an aldimine-containing compound of the formula (I) AC8 and AC9, show only a slight viscosity increase during storage. During their use, they cure rapidly and without bubble formation, are odorless and, in the cured state, have good mechanical properties.

One-Component Plastic Precursors Which can be Used as Adhesives

Examples 28 to 35 and Example 36

Comparison

For each of the examples, the substances shown in table 6, in the stated amount (in parts by weight), were processed in a vacuum mixer in the absence of moisture to give a lump-free, homogeneous paste, and the latter was immediately filled into an internally coated aluminum cartridge and the cartridge was closed air-tight. The polyurethane polymers PP1 and PP2 were prepared as described in the case of example 16 and example 26, respectively.

The polyaldimine PA1 was prepared from the condensation reaction between 1,6-hexamethylenediamine and 2,2-dimethyl-3-lauroyloxypropanal (in the molar ratio of 1:1.05 between amino and aldehyde groups) and had an amine content of 2.94 mmol $NH_2$/g.

The polyaldimine PA2 was prepared from the condensation reaction between alpha,omega-polyoxypropylenediamine (Jeffamine® D-230, Huntsman; amine content=8.29 mmol $NH_2$/g) and 2,2-dimethyl-3-lauroyloxypropanal (in the molar ratio of 1:1.05 between amino and aldehyde groups) and had an amine content of 2.50 mmol $NH_2$/g.

The ratio between the isocyanate groups in the polyurethane polymer and the sum of the reactive groups (aldimino groups plus amino and hydroxyl groups) in the aldimine-containing compounds of the formula (I), the aldimines of the formula (XI) and the polyaldimines is 1.0/0.7 for all examples.

The adhesives thus obtained were tested with regard to skin formation time, odor and mechanical properties after curing and with regard to adhesion properties on glass. The results of the tests are shown in table 7.

The Shore A hardness was determined according to DIN 53505.

Schweiz AG) for each measurement. After drying for 10 minutes in air, the small plates were arranged with the aid of a suitable PTFE mold at a vertical distance of 5 mm relative to one another so that they overlapped at the top ends by 10 mm. The overlap region between the small plates was filled with adhesive, the latter coming to rest on the activated sides of the small plates. The adhesive was cured for 7 days at 23° C. and 50% relative humidity, and breaking force was then determined with the aid of a tensile tester at a constant crossbeam speed of 20 mm/min according to DIN EN 1465. The stated values are mean values of three measurements.

The adhesion on glass was determined on the basis of the fracture pattern on the test specimen used for determining the tensile shear strength, after the test was complete. A 100% cohesive fracture, i.e. taking place completely in the adhesive, was rated with the value "1", while a 0% cohesive fracture, i.e. taking place completely between glass surface and adhesive and therefore an adhesive fracture, was rated with the

TABLE 6

Composition of adhesives.

| | Example | | | | | | | | |
|---|---|---|---|---|---|---|---|---|---|
| | 28 | 29 | 30 | 31 | 32 | 33 | 34 | 35 | 36 (comp.) |
| Polyurethane polymer | PP1, 50.0 | PP1, 50.0 | PP1, 50.0 | PP2, 50.0 | PP2, 50.0 | PP2, 50.0 | PP2, 50.0 | PP2, 50.0 | PP1, 50.0 |
| Aldimine(s) of the formula (XI) | AL1, 3.3 | AL2, 3.9 | AL6, 3.9 | AL1, 1.8; AL3, 1.9 | AL4, 1.9 | — | — | — | AL8, 2.5 |
| Aldimine-containing compound of the formula (I)$^a$ | — | — | — | — | — | AC1, 2.6 | AC2, 3.0 | AC3, 2.5 | — |
| Polyaldimine | — | — | — | — | PA1, 2.9 | PA2, 3.7 | PA2, 2.5 | PA1, 2.9 | — |
| Plasticizer$^b$ | 12.2 | 11.6 | 11.6 | 11.8 | 10.7 | 9.9 | 10.6 | 10.7 | 13.0 |
| Kaolin | 17.0 | 17.0 | 17.0 | 17.0 | 17.0 | 17.0 | 17.0 | 17.0 | 17.0 |
| Carbon black | 17.0 | 17.0 | 17.0 | 17.0 | 17.0 | 17.0 | 17.0 | 17.0 | 17.0 |
| Drying agent$^c$ | 0.1 | 0.1 | 0.1 | 0.1 | 0.1 | 0.1 | 0.1 | 0.1 | 0.1 |
| Epoxysilane$^d$ | 0.3 | 0.3 | 0.3 | 0.3 | 0.3 | 0.3 | 0.3 | 0.3 | 0.3 |
| Catalyst$^e$ | 0.1 | 0.1 | 0.1 | 0.1 | 0.1 | 0.1 | 0.1 | 0.1 | 0.1 |

$^a$aldimine-containing compound of the formula (I).
$^b$diisodecyl phthalate (DIDP; Palatinol ® Z, BASF).
$^c$p-tosyl isocyanate.
$^d$3-glycidyloxypropyltrimethoxysilane (Silquest ® A-187, OSi Crompton).
$^e$salicylic acid (5% by weight in dioctyl adipate).

For testing the tensile shear strength, in each case 2 small glass plates of 6 mm thickness, 25 mm width and 75 mm length (Floatglas; from Rocholl, Schönbrunn, Germany) were pretreated with Sika® activator (obtainable from Sika value "5". Adhesions having cohesive fracture values of less than 75% are considered to be inadequate.

The remaining tests were carried out as described in the case of example 16.

TABLE 7

Properties during and after curing of the adhesives
Composition of adhesives.

| | Example | | | | | | | | |
|---|---|---|---|---|---|---|---|---|---|
| | 28 | 29 | 30 | 31 | 32 | 33 | 34 | 35 | 36 (comp.) |
| Skin formation time$^a$ | 23 | 27 | 18 | 40 | 60 | 68 | 80 | 50 | 90 |
| Odor | none | none | none | none | none | none | none | none | strong |
| Shore A hardness | 53 | 60 | 58 | 54 | 65 | 56 | 56 | 66 | 56 |

TABLE 7-continued

Properties during and after curing of the adhesives
Composition of adhesives.

| | Example | | | | | | | | |
|---|---|---|---|---|---|---|---|---|---|
| | 28 | 29 | 30 | 31 | 32 | 33 | 34 | 35 | 36 (comp.) |
| Tensile strength (MPa) | 9.7 | 9.9 | 9.9 | 10.2 | 9.1 | 8.1 | 9.0 | 7.0 | 9.6 |
| Elongation at break (%) | 650 | 590 | 530 | 720 | 530 | 700 | 650 | 450 | 550 |
| Modulus of elasticity (MPa)[b] | 3.6 | 4.6 | 4.0 | 3.3 | 7.3 | 4.1 | 4.0 | 9.0 | 4.0 |
| Tensile shear strength[c] | 8.6 | 7.5 | 10.1 | 9.9 | 8.5 | 6.3 | 6.7 | 6.4 | 3.9 |
| Adhesion on glass | 1 | 1 | 1 | 1 | 1 | 1 | 1 | 1 | 5 |

[a] in minutes.
[b] at 0.5-5.0% elongation.
[c] in MPa.

Table 7 shows that the adhesives of examples 28 to 35, which contain aldimine-containing compounds of the formula (I) which were prepared in examples 28 to 32 in the course of the adhesive preparation (in situ) from aldimines of the formula (XI) and the polyurethane polymers PP1 or PP2, and prepared beforehand in examples 33 to 35 and, in some case in combination with polyaldimines, were mixed into the adhesive, cure rapidly, are odorless and, in the cured state, have very good mechanical properties. In contrast, the adhesive of comparative example 36, which contains an aldimine-containing compound according to the prior art, which was prepared in situ from the aldimine AL8 and the polyurethane polymer PP1, cures more slowly, has a strong odor and has insufficient adhesion to glass.

The invention claimed is:

1. An aldimine-containing compound of the formula (I)

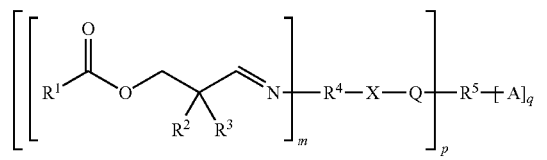

(I)

in which m is an integer from 1 to 4, p is an integer from 1 to 6 and q is an integer from 0 to 5, with the proviso that p+q is from 2 to 6;

and in which $R^1$ either is a monovalent hydrocarbon radical having 6 to 30 C atoms which optionally has at least one heteroatom, or is a substituent of the formula (II)

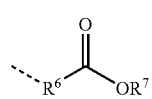

(II)

in which $R^6$ is a divalent hydrocarbon radical having 2 to 20 C atoms which optionally has at least one heteroatom, and $R^7$ is a monovalent hydrocarbon radical having 1 to 20 C atoms;

and in which $R^2$ and $R^3$ either, independently of one another, are each a monovalent hydrocarbon radical having 1 to 12 C atoms;

or together form a divalent hydrocarbon radical having 4 to 20 C atoms which is part of an optionally substituted, carbocyclic ring having 5 to 8, preferably 6, C atoms;

and in which $R^4$ is an (m+1)-valent hydrocarbon radical which has 2 to 12 C atoms and optionally contains at least one heteroatom;

and in which

X is O, S or N—$R^8$, in which $R^8$ either is a monovalent hydrocarbon radical which has 1 to 20 C atoms and optionally has at least one carboxylic acid ester, nitrile, nitro, phosphonic acid ester, sulfone or sulfonic acid ester group, or is a substituent of the formula (III)

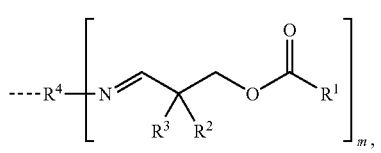

(III)

and in which

A is a reactive group selected from the group consisting of

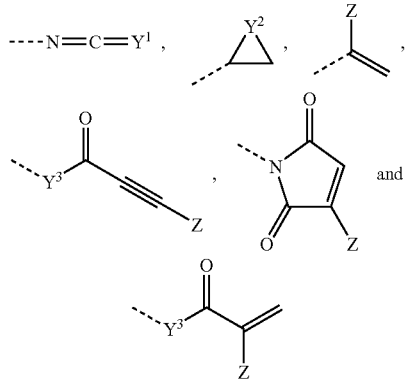

in which
Y$^1$ is O or S, Y$^2$ is O, S or N—H, Z is H or CH$_3$ and Y$^3$ is O or N—H;
and
R$^5$ either
is a (p+q)-valent organic radical optionally containing heteroatoms, as obtained by removing p+q radicals A from R$^5$—[A]$_{p+q}$,
or
is N, NR$^{14}$, O, OC(C)O, Si, P(O)O$_3$ or SO$_2$,
in which
R$^{14}$ is a monovalent hydrocarbon radical having 1 to 20 C atoms;
and
Q is a substituent which is selected from the group consisting of

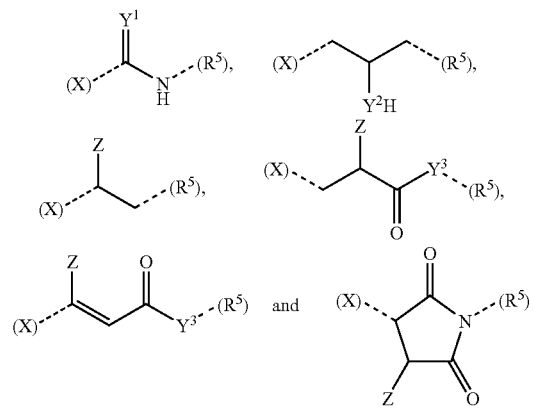

in which the dashed lines are the bonds to the stated substituents.

2. The aldimine-containing compound as claimed in claim 1, wherein R$^2$ and R$^3$ are identical.

3. The aldimine-containing compound as claimed in claim 1, wherein m is 2 or 1.

4. The aldimine-containing compound as claimed in claim 1, wherein X is N—R$^8$ and R$^8$ is a monovalent hydrocarbon radical of the formula (IX) or (IX')

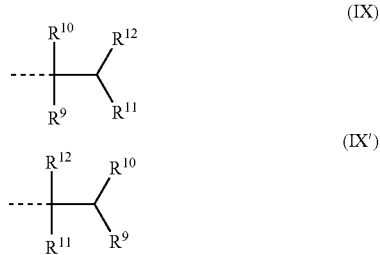

in which R$^9$ is a radical which is selected from the group consisting of —COOR$^{13}$, —CN, —NO$_2$, —PO(OR$^{13}$)$_2$, —SO$_2$R$^{13}$ and —SO$_2$OR$^{13}$;
R$^{10}$ is a hydrogen atom or a radical selected from the group consisting of —R$^{13}$, —COOR$^{13}$ and —CH$_2$COOR$^{13}$ and
R$^{11}$ and R$^{12}$, independently of one another, are a hydrogen atom or a radical selected from the group consisting of —R$^{13}$, —COOR$^{13}$ and —CN, in which R$^{13}$ is a monovalent hydrocarbon radical having 1 to 20 C atoms.

5. The aldimine-containing compound as claimed in claim 1, wherein X is O or S.

6. The aldimine-containing compound as claimed in claim 1, wherein it is prepared by reacting an aldimine of the formula (XI) with a compound D of the formula (XII) having the reactive groups A and A'

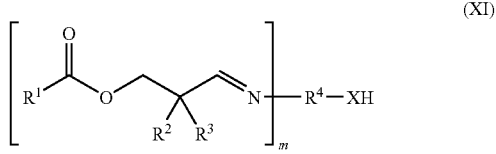

in which A' is a reactive group which is selected from the group consisting of

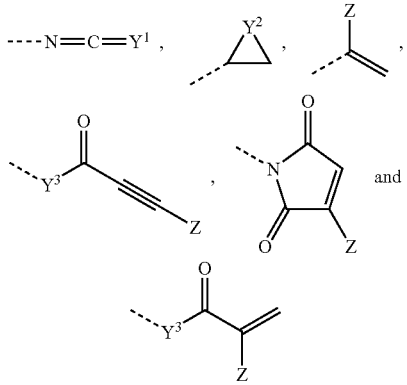

and in which A' may be identical to the reactive group A or different therefrom.

7. The aldimine-containing compound as claimed in claim 6, wherein the compound D is a polyisocyanate.

8. The aldimine-containing compound as claimed in claim 6, wherein the compound D is a polyepoxide.

9. The aldimine-containing compound as claimed in claim 6, wherein the compound D is a poly(meth)acrylate.

10. The aldimine-containing compound as claimed in claim 6, wherein the aldimine of the formula (XI) is used in a ratio of one mole equivalent of active hydrogen of the aldimine to one mole equivalent of reactive groups of the compound D.

11. The aldimine-containing compound as claimed in claim 6, wherein the aldimine of the formula (XI) is used in a ratio of less than one mole equivalent of active hydrogen of the aldimine to one mole equivalent of reactive groups of the compound D.

12. The aldimine-containing compound as claimed in claim 6, wherein the reactive group A is different from the reactive group A'.

13. A method for making an aldehyde of the formula (IV)

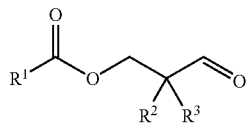

(IV)

comprising hydrolytically deprotecting the aldimine-containing compound of the formula (I) of claim 1.

14. A process for the hydrolysis of an aldimine-containing compound as claimed in claim 1.

15. A process for the crosslinking of an aldimine-containing compound as claimed in claim 1, wherein the product of m and p of the formula (I) gives a value of q or less, under the influence of water.

16. A composition containing an aldimine-containing compound as claimed in claim 1.

17. The aldimine-containing compound as claimed in claim 1, wherein $R^1$ is ether oxygen.

18. The aldimine-containing compound as claimed in claim 1, wherein $R^6$ is ether oxygen.

19. The aldimine-containing compound as claimed in claim 1, wherein $R^4$ is ether oxygen or tertiary amine nitrogen.

20. The aldimine-containing compound as claimed in claim 2, wherein $R^2$ and $R^3$ are each a methyl group.

21. The aldimine-containing compound as claimed in claim 3, wherein m is 1.

* * * * *